(12) United States Patent
Thompson et al.

(10) Patent No.: US 11,981,631 B2
(45) Date of Patent: May 14, 2024

(54) PROCESSES FOR CONVERTING ALKYNE TO OLEFIN

(71) Applicant: ExxonMobil Chemical Patents Inc., Baytown, TX (US)

(72) Inventors: Mark D. Thompson, Sarnia (CA); David R. Slim, Sarnia (CA); Grant H. Schumacher, Houston, TX (US); Mark A. Nierode, Kingwood, TX (US); May-Ru Chen, Houston, TX (US); David B. Looney, Houston, TX (US); Keng-Fai Kuan, Singapore (SG); Mary M. Rethwisch, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 56 days.

(21) Appl. No.: 17/578,041

(22) Filed: Jan. 18, 2022

(65) Prior Publication Data

US 2022/0242806 A1 Aug. 4, 2022

Related U.S. Application Data

(60) Provisional application No. 63/144,518, filed on Feb. 2, 2021.

(51) Int. Cl.
*C07C 5/09* (2006.01)
*B01J 23/44* (2006.01)

(52) U.S. Cl.
CPC ............... *C07C 5/09* (2013.01); *B01J 23/44* (2013.01); *C07C 2523/44* (2013.01)

(58) Field of Classification Search
CPC ......... C07C 5/09; C07C 2523/44; B01J 23/44
See application file for complete search history.

(56) References Cited

U.S. PATENT DOCUMENTS 3,412,174 A * 11/1968 Kroll .................... C07C 209/48
585/277
3,763,268 A * 10/1973 Chappel ................... C07C 5/02
208/143
9,714,204 B1 * 7/2017 Drew .......................... C10J 3/72

\* cited by examiner

*Primary Examiner* — In Suk C Bullock
*Assistant Examiner* — Jason Y Chong

(57) ABSTRACT

Disclosed are processes for converting an alkyne to an olefin comprising feeding a molecular-oxygen-containing gas stream into a converting zone of an alkyne converter along with an alkyn-containing feed mixture comprising hydrocarbons and molecular hydrogen to contact the converting catalyst. The converting catalyst can be regenerated online as a result.

19 Claims, 1 Drawing Sheet

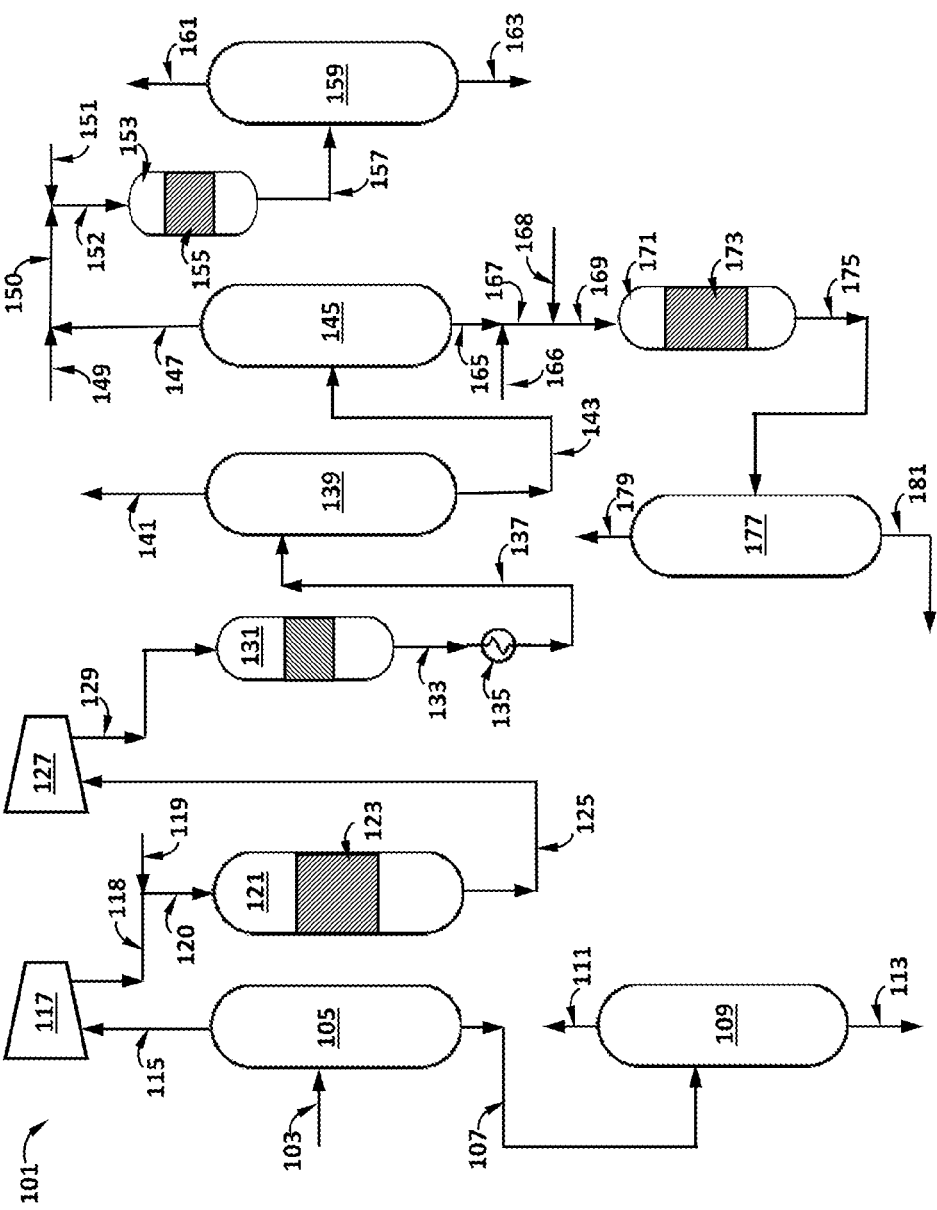

PROCESSES FOR CONVERTING ALKYNE TO OLEFIN

CROSS-REFERENCE TO RELATED APPLICATION

This application claims priority to and the benefit of U.S. Provisional Application No. 63/144,518 having a filing date of Feb. 2, 2021, the disclosure of which is incorporated herein by reference in its entirety.

FIELD

This disclosure relates to processes for converting an alkyne to an olefin by hydrogenation. In particular, this disclosure relates to processes for converting a mixture comprising an alkyne, an olefin, and molecular hydrogen in the presence of a converting catalyst in a converting zone to convert at least a portion of the alkyne to the olefin. The processes of this disclosure are useful for, e.g., producing high-purity ethylene and propylene products in an olefins production plant.

BACKGROUND

Olefinic compounds are a class of hydrocarbon compounds which have at least one double bond of four shared electrons between two carbon atoms. In part as a result of their utility as feeds for producing desirable products, olefin demand continues to grow, particularly for light olefin such as ethylene, propylene, and butenes.

Light olefin is typically manufactured in an olefins production plant (e.g., an ethylene plant) which includes production and recovery facilities. In certain conventional olefins plants, the olefin production facility includes one or more steam cracker furnaces for steam cracking hydrocarbon-containing feeds. A steam cracker furnace generally includes a convection section and a radiant section. The radiant section includes a plurality of tubular members which are typically referred to as "radiant tubes". The radiant tubes are located proximate to one or more fired heaters, e.g., burners, in the radiant section which heat the outer surface of the furnace tubes. Hot combustion gases exit the radiant section and are introduced into the convection section. The convection section also includes tubular members, typically referred to as "convection tubes". The hot gases from the radiant section heat the outer surfaces of the convection tubes and then exit the convection section.

Conventional steam cracking processes typically produce light olefins by hydrocarbon pyrolysis during pyrolysis mode. During pyrolysis mode, a hydrocarbon-containing feed is introduced into the convection tubes for feed preheating. Feed preheating is carried out in segments of the convection tubes located in an upper region of the convection section. Steam is combined with the preheated feed, and the steam-feed mixture is further heated in segments of the convection tubes located in a lower region of the convection section. The heated feed-steam mixture is introduced into the heated furnace tubes in the radiant section, and heat transferred from the furnace tube to the mixture results in the pyrolysis of at least a portion of the feed to produce a steam cracker effluent comprising light hydrocarbons including the desired light olefins. The steam cracker effluent is typically quenched and then separated to obtain various fractions including a process gas stream comprising C5- hydrocarbons, a steam cracker naphtha stream, a steam cracker gas oil stream, and a steam cracker tar stream. In the product recovery section of the olefins production plant, the process gas stream, upon compression, can be cooled and separated to recover various streams, including a C5 hydrocarbon stream, a C4 hydrocarbon stream, a propylene product stream, a propane stream which can be at least partly recycled to the steam cracker, an ethylene product stream, an ethane stream which can be at least partly recycled to the steam cracker, a tail gas stream comprising methane and molecular hydrogen, and optionally a molecular hydrogen stream.

Saleable ethylene and propylene products are routinely required to meet various specifications for their intended use. For example, an ethylene product intended for producing polyethylene in an ethylene polymerization reactor may be required to contain acetylene at no more than 2 ppm by mole, based on the total moles of ethylene in the product, and a propylene product intended for producing polypropylene in a propylene polymerization reactor can be required to contain methylacetylene and propadiene, in total, at no more than 1% by weight, based on the total moles of propylene in the product.

While steam crackers are generally optimized to produce the desirable ethylene and propylene molecules at high yields, and produce the undesirable acetylene, and methylacetylene and/or propadiene ("MAPD") at low yields, the steam cracker effluent, and the downstream process gas stream, tend to comprise acetylene and MAPD at non-negligible quantities. Without a step of abating acetylene in the recovery section in the olefins production plant, the ethylene product stream can be contaminated by acetylene at a level exceeding the specification required for the ethylene product. Similarly, without a step of abating MAPD in the recovery section, the propylene product stream can be contaminated by MAPD at a level exceeding the specification required for the propylene product. As such, the recovery section of an olefins production plant typically includes at least one acetylene converter which receives an acetylene-, ethylene-, and molecular hydrogen-containing stream, enables selective conversion of acetylene to ethylene in the presence of a converting catalyst, and produces a converted effluent comprising acetylene at an abated level. Likewise, the recovery section may also include a MAPD converter which receives a MAPD- and molecular hydrogen-containing stream, enables selective conversion of MAPD to propylene in the presence of a converting catalyst, and produces a converted effluent comprising MAPD at an abated level.

The converting catalysts used in the acetylene converter and the MAPD converter typically comprises a hydrogenation metal such as nickel, palladium, and the like. High performance of the converting catalysts such as high activity and selectivity, broad operation windows, and long catalyst service life, are highly desired. Modern converting catalysts, especially those comprising palladium, can be highly selective and robust. Nonetheless, contaminants such as coke and heavy hydrocarbons can form and accumulate on the converting catalyst over time, gradually reducing its performance. In addition, contaminants in the feed, including but not limited to nitrogen-containing compounds, phosphorous-containing compounds, arsenic-containing compounds, sulfur-containing compounds, halogen-containing compounds, mercury-containing compounds, alkali metal elements, and the like, can poison the converting catalyst, resulting in temporary or permanent reduction of performance.

Molecular oxygen, if present in the feed mixture to the acetylene converter or the MAPD converter, has been known generally as an undesirable poison to the converting catalyst in the art. One perceived detriment of molecular oxygen is its oxidation of the metal in the converting catalyst resulting in reduced catalyst activity, and its oxidation of useful and abundant molecules such as ethylene and propylene, catalyzed by the converting catalyst, to produce $CO_2$, which could cause the ethylene or propylene product to exceed the required $CO_2$ specification. Another concern is the potential oxidation of molecular hydrogen producing water which may require costly abatement. A more significant concern is a potentially large exotherm from the oxidation reactions, which could result in undesirable temperature increase in the catalyst bed, resulting in runaway of the converter and forced shut-down. Therefore, conventionally, molecular oxygen ingress into the acetylene converter and the MAPD converter are generally regarded as highly undesirable.

As a result of the accumulation of contaminants and poisons, the converting catalyst can gradually lose activity and/or selectivity. To compensate, the inlet temperature can be increased in order to maintain the outlet concentration of acetylene or MAPD at a threshold level. A run of the converter is terminated when the inlet temperature reaches the upper limit of the operating envelope and the converter is no longer able to maintain the outlet acetylene/MAPD specification, or converter selectivity has degraded below a threshold level. The converting catalyst may be taken out of the converter, regenerated ex-situ to partly restore its activity and/or selectivity, and then reloaded into the converter. The converting catalyst may also undergo regeneration while remaining inside the reaction vessel, typically by disconnecting the converter inlet and outlet, and connecting to regeneration equipment. During regeneration, the offline converting catalyst is typically heated to an elevated temperature in the presence of air to burn off the coke, heavy hydrocarbon, and certain poisons. Maintaining converting the hydrocarbon feed mixture while regenerating the converting catalyst online was impossible pursuant to such industry normal practice.

There remains a need to improve the processes for converting acetylene into ethylene and MAPD into propylene in the acetylene converter and the MAPD converter, especially the performance of the converting catalyst, desirably without interrupting the ethylene or propylene production processes. This disclosure satisfies this and other needs.

SUMMARY

We have surprisingly discovered that by introducing molecular oxygen into an acetylene converter, along with the feed mixture comprising C1-C3 hydrocarbons and molecular hydrogen, the performance of the converting catalyst can be significantly enhanced without interrupting the normal operation of the acetylene converter. Such oxygen introduction can be conducted safely and in a controlled manner without causing temperature excursion and process shut-down. The $CO_2$ concentration in the converted effluent exiting the converter can be controlled within a desired threshold level, notwithstanding a potential increase thereof resulting from the molecular oxygen introduction. In effect, we have for the first time unexpectedly achieved safe online regeneration of a converting catalyst in an acetylene converter without interrupting the operation of the acetylene converter, enabling a prolonged catalyst life and significant cost savings. It is believed the same process can be effectively carried out for a MAPD converter and other alkyne converters.

Thus, one aspect of this disclosure relates to processes for converting an alkyne to an olefin, the process comprising one or more of the following: (1) supplying a feed mixture comprising the alkyne, the olefin, and molecular hydrogen into a converting zone; (2) supplying a molecular-oxygen-containing gas stream into the converting zone; and (3) during an oxidation interval, contacting the feed mixture and the molecular oxygen with a converting catalyst in the converting zone, wherein the converting catalyst is contaminated by one or more of coke, a heavy hydrocarbon, a poison comprising one or more of: arsenic and/or a compound thereof (e.g., $AsH_3$), mercury and/or a compound thereof, a nitrogen-containing compound (e.g., amines), a phosphorous-containing compound (e.g., a phosphine), a sulfur-containing compound (e.g., COS, $H_2S$, and $CH_3SH$), a halogen-containing compound (e.g., a chlorine-containing compound), a transition metal (e.g., Fe, Mn, Pb, Ti) and/or a compound thereof, an alkali metal (e.g., Li, Na, K) and/or a compound thereof, and an alkaline earth metal (e.g., Mg, Ca) and/or a compounds thereof, to convert at least a portion of the alkyne to the olefin, and to enhance the converting catalyst.

A second aspect of this disclosure relates to processes for converting an alkyne to an olefin, the process comprising one or more of the following: (i) supplying a feed mixture comprising the alkyne, the olefin, an optional catalyst poison, and molecular hydrogen into a converting zone; (ii) supplying a molecular-oxygen-containing gas stream into the converting zone; (iii) contacting the feed mixture and the molecular oxygen with the converting catalyst in the converting zone under converting conditions to produce a converted effluent exiting the converting zone and to prevent, reduce, or delay the contamination of the converting catalyst by one or more of coke, a heavy hydrocarbon, and the optional catalyst poison.

Still a third aspect of this disclosure relates to processes for converting an alkyne to an olefin, the process comprising one or more of the following: (I) during a first hydrogenation interval, supplying a feed mixture into a converting zone through a feed inlet, where the feed mixture comprises the alkyne, the olefin, and molecular hydrogen, and the feed mixture is essentially free of molecular oxygen; (II) during the first hydrogenation interval, contacting the feed mixture with a converting catalyst comprising a hydrogenation metal (preferably Pd) under converting conditions in the converting zone to convert at least a portion of the alkyne to the olefin to produce a first converted effluent exiting the converting zone; (III) during an oxidation interval after the first hydrogenation interval, supplying a molecular-oxygen-containing gas stream and the feed mixture into the converting zone; and (IV) during the oxidation interval, contacting the feed mixture and the molecular oxygen with the converting catalyst in the converting zone to enhance the converting catalyst and to produce a second converted effluent exiting the converting zone.

BRIEF DESCRIPTION OF THE DRAWING

The FIGURE is a schematic illustration of a partial process flow of the recovery section of an olefins production plant including a de-propanizer, a front-end acetylene converter, a de-methanizer, a de-ethanizer, a trim converter, and a MAPD converter, among others, in which various embodiments of the processes of this disclosure may be implemented.

DETAILED DESCRIPTION

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same as or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

As used herein, the indefinite article "a" or "an" shall mean "at least one" unless specified to the contrary or the context clearly indicates otherwise. Thus, embodiments using "an alkyne converter" include embodiments where one, two or more alkyne converters are used, unless specified to the contrary or the context clearly indicates that only one alkyne converter is used.

The term "hydrocarbon" as used herein means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C1 to C3 hydrocarbon" or "C1-C3 hydrocarbon" can be any of methane, ethane, ethylene, acetylene, propane, propylene, methylacetylene, propadiene, cyclopropane, and any mixtures of two or more thereof at any proportion between and among the components. A "saturated C2-C3 hydrocarbon" can be ethane, propane, cyclopropane, or any mixture of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" or ""Cm to Cn hydrocarbon stream" means a hydrocarbon stream consisting essentially of Cm-Cn hydrocarbon(s).

The term "crude" as used herein means whole crude oil as it flows from a wellhead, a production field facility, a transportation facility, or other initial field processing facility, optionally including crude that has been processed by a step of desalting, treating, and/or other steps as may be necessary to render it acceptable for conventional distillation in a refinery. Crude, as used herein, is presumed to contain resid. The term "crude fraction", as used herein, means a hydrocarbon fraction obtained via the fractionation of crude.

The term "olefin product" as used herein means a product that includes an alkene, preferably a product consisting essentially of one or more alkenes. An olefin product in the meaning of this disclosure can be, for example, an ethylene stream, a propylene stream, a butylene stream, an ethylene/propylene mixture stream, and the like.

The term "alkyn" means an organic compound having a carbon-carbon triple bond therein. The term "olefin" means an organic compound having a carbon-carbon double bond therein. The term "ethylene" means ethene; "propylene" means prop-1-ene; "acetylene" means ethyne; "methylacetylene" means prop-1-yne; "propadiene" means propa-1,2-diene, an isomer of methylacetylene; and "MAPD" means methylacetylene, propadiene, or any mixture thereof.

The term "alkyne converter" means a reactor in which an alkyne is selectively converted to an olefin in the presence of molecular hydrogen and a converting catalyst. The term "front-end converter" means an alkyne converter receiving a feed mixture stream produced from an upstream separation column that comprises substantial quantity of methane and molecular hydrogen. The term "back-end converter" means an alkyne converter receiving a hydrocarbon mixture stream produced from an upstream separation column that is substantially free of methane and molecular hydrogen.

The term "consisting essentially of" as used herein means the composition, feed, effluent, product, or stream includes a given component at a concentration of at least 60 mol %, preferably at least 70 mol %, more preferably at least 80 mol %, more preferably at least 90 mol %, still more preferably at least 95 mol %, based on the total weight of the composition, feed, effluent, product, or other stream in question.

The term "rich" when used in phrases such as "X-rich" or "rich in X" means, with respect to an outgoing stream obtained from a device, that the stream comprises material X at a concentration higher than in the feed material fed to the same device from which the stream is derived.

The term "inlet temperature" means the temperature of a feed mixture at the inlet through which the feed mixture enters a vessel, a reactor, or a converting zone.

As used herein, "wt %" means percentage by weight, "vol %" means percentage by volume, "mol %" means percentage by mole, "ppm" means parts per million, and "ppm wt" "wppm", and "ppm by weight" are used interchangeably to mean parts per million on a weight basis. All concentrations herein are expressed on the basis of the total amount of the composition in question, unless specified otherwise. Thus, the concentrations of the various components of the "feed mixture" are expressed based on the total weight of the feed mixture. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

The processes of this disclosure generally relates to any alkyne conversion process in which one or more alkyne is converted into olefin(s) in the presence of molecular hydrogen and a converting catalyst. While the description of the processes below focuses on acetylene conversion in an acetylene converter and MAPD conversion in a MAPD converter in an olefins production plant, the disclosure herein is not limited to acetylene conversion and MAPD conversion. For example, the processes of this disclosure can be used for converting heavier alkynes, e.g., but-1-yn, but-2-yn, methylpropadiene, and mixtures thereof.

The processes of this disclosure generally comprises an oxidation interval during which a molecular oxygen-containing gas stream is intentionally introduced into a converting zone along with a feed mixture comprising the alkyne intended for conversion and molecular hydrogen, where the feed mixture and the molecular oxygen contacts the converting catalyst in the converting zone. The contacting can result in one or more of (i) the enhancement of the converting catalyst, (ii) preventing or delaying the deactivation of the converting catalyst, and (iii) a longer life cycle of the converting catalyst.

The processes of this disclosure may or may not include a hydrogenation interval during which only a feed mixture comprising the alkyne intended for conversion and molecular hydrogen is supplied into the converting zone, and the molecular oxygen-containing gas stream is not supplied into the converting zone.

In various embodiments, the molecular-oxygen-containing gas stream can be selected from (a) pure $O_2$; (b) pure $O_3$; (c) air; (d) a mixture of $O_2$ with one or more inert gas (e.g., $N_2$, $CH_4$, $C_2H_6$, $C_3H_6$, $CO_2$, $H_2O$, He, Ne, Ar, Kr, and the like, and mixtures thereof); and (e) a mixture of two or more of (a), (b), (c), and (d). In this disclosure, "molecular oxygen" means $O_2$, $O_3$, or mixtures thereof, preferably $O_2$. The molecular-oxygen-containing gas stream can comprise molecular oxygen at any suitable concentration, e.g., from 10 ppm (or 100 ppm, 500 ppm, 1000 ppm, 5000 ppm) by mole to 30 (or 1, 5, 10, 15, 20, 25) mol %, or to 70 (or 35, 40, 45, 50, 55, 60, 65) mol %, or to 100 (or 75, 80, 90, 95) mol %, based on the total moles of molecules in the molecular-oxygen-containing gas stream. A preferred molecular-oxygen-containing gas stream comprises molecular oxygen from 5 (or 6, 8, 10, 12, 14, 15) to 25 (or 16, 18, 20, 22, 24) mol %, based on the total moles of molecules in the molecular-oxygen-containing gas stream. A particularly preferred molecular-oxygen-containing gas stream is air. Another preferred molecular-oxygen-containing gas stream is a stream of $O_2$ and $N_2$ mixture, preferably comprising from, e.g., 5, 6, 7, 8, or 9 mol %, to 10, 12, 14, 15, 16 mol %, to 17, 18, 19, 20, 22, 24, 25 mol %, of $O_2$, based on the total moles of $O_2$ and $N_2$ in the gas stream. Limiting the molecular oxygen concentration in the gas mixture to ≤25 mol % has the advantage of controlling, reducing, or preventing undesirable oxidation reactions between the molecular oxygen with hydrocarbon(s) and/or molecular hydrogen at the inlet of the molecular-oxygen gas stream, and the undesirable potential exotherm and even explosion associated with such oxidation reactions when molecular oxygen is introduced at an overly high concentration.

While it is possible to introduce the molecular-oxygen-containing gas stream directly into the converting zone as a separate stream via a dedicated inlet, preferably, the molecular-oxygen-containing gas stream is first injected into the feed mixture to form a molecular-oxygen-containing feed mixture, which is then fed into the converting zone. Such pre-mixing of the oxygen-containing gas stream with the feed mixture can achieve a more even distribution of molecular oxygen in the converting zone, avoiding potential hot spot in the converting zone caused by uneven distribution of molecular oxygen, while promoting broader and more even enhancement or protection of the converting catalyst.

The contacting time of the feed mixture and molecular oxygen with the converting catalyst (i.e., the duration of the oxidation interval) can vary broadly from, e.g., 1 minute to multiple years. For the purpose of regenerating the converting catalyst poisoned by one or more of arsenic and compounds thereof (e.g., $AsH_3$), mercury and compounds thereof, nitrogen-containing compounds (e.g., amines), phosphorous-containing compounds (e.g., phosphines), sulfur-containing compounds (e.g., COS, $H_2S$, and $CH_3SH$), halogen-containing compounds (e.g., chlorine-containing compounds), transition metals (e.g., Fe, Mn, Pb, Ti) and compounds thereof, alkali and alkaline earth metals and compounds thereof, and the like, the duration of the oxidation interval can be relatively short to achieve appreciable enhancement of catalyst activity and/or selectivity, ranging from, e.g., 1, 3, 4, 5, 6, 7, 8, 9, 10, 15, 20, 25, 30, 35, 40, 45, 50, 55, 60 minutes to, e.g., 2, 3, 4, 5, 6, 7, 8, 9, 10, 12, 14, 15, 16, 18, 20, 22, 24 hours, to, e.g., 2, 3, 4, 5, 6, 7, 8, 9, 10 days. For the purpose of regenerating the converting catalyst contaminated by heavy hydrocarbons and coke, the duration of the oxidation interval can be relatively long, ranging from, e.g., 1, 2, 3, 4, 5, 6, 7 days to, e.g., 2, 3, 4, 5, 6, 7, 8 weeks. For the purpose of protecting the converting catalyst from contamination by poisons, coke, heavy hydrocarbons and prolonging the catalyst cycle life, one may run the oxidation interval for any arbitrary period such as weeks, months, or years, and even the whole operation campaign of the catalyst batch.

The amount of molecular oxygen supplied into the converting zone can vary broadly from, e.g., 0.01, 0.02, 0.04, 0.05, 0.06, 0.08, 0.10, 0.15, 0.20, 0.25, 0.30, 0.35, 0.40, 0.45, 0.50, 0.60, 0.70, 0.80, 0.90 ppm by mole, to, e.g., 1.0, 2.0, 3.0, 4.0, 5.0, 6.0, 7.0, 8.0, 9.0 ppm by mole, to, e.g., 10, 12, 14, 15, 16, 18, 20, 22, 24, 25, 26, 28, 30 ppm by mole, to, e.g., 35, 40, 45, 50, 55, 60 ppm by mole, to, e.g., 65, 70, 75, 80, 85, 90, 95, 100 ppm by mole of molecular oxygen ($O_2$ preferred) based on the total moles of molecules in the molecular-oxygen-containing feed mixture supplied into the converting zone through the inlet. The lower the molecular oxygen concentration in the total feed mixture supplied into the converting zone, the longer it can take to enhance a contaminated/poisoned converting catalyst to a desired predetermined level. If the molecular oxygen concentration in the total feed mixture fed supplied into the converting zone is too high, however, undesirable oxidation of hydrocarbons such as the desired olefins and even a temperature excursion may occur. Thus, preferred molecular oxygen concentration in the total feed mixture supplied into the converting zone ranges from, e.g., 0.25, 0.30, 0.30, 0.35, 0.40, 0.45, 0.50, 0.60, 0.70, 0.80, 0.90 ppm by mole, to, e.g., 1.0, 2.0, 3.0, 4.0, 5.0, 6.0, 7.0, 8.0, 9.0 ppm by mole, to, e.g., 10, 12, 14, 15, 16, 18, 20, 22, 24, 25, 26, 28, 30 ppm by mole, to, e.g., 35, 40, 45, 50, 55, 60 ppm by mole, to, e.g., 65, 70, 75, 80 ppm by mole, based on the total moles of molecules in the total feed mixture supplied into the converting zone. In certain embodiments, after implementing the oxidation interval and the converting catalyst has been regenerated to a desired degree, the supply of the molecular-oxygen-containing gas stream can be stopped to initiate a new hydrogenation interval, allowing the alkyne conversion at a high catalyst activity and selectivity. Indeed, the oxidation interval can be implemented repeatedly, e.g., after whenever an unexpected decrease of the converting catalyst is detected.

In certain embodiments of the processes of this disclosure, during the hydrogenation interval, the performance of the converting catalyst can be monitored. Where an unexpected decrease of performance of the converting catalyst is observed, the hydrogenation interval may be stopped. Such unexpected decrease of performance of the converting catalyst can be manifested as (a) an increase of inlet temperature of ≥5° C. within a period of ≤24 hours while maintaining substantially constant alkyne concentration in the converted effluent; and/or (b) a temperature excursion resulting in reactor trip. Such unexpected decrease of catalyst performance is usually indicator of abrupt poisoning of the converting catalyst. Thus, in certain embodiments, immediately after the stoppage of the hydrogenation interval, an oxidation interval starts, i.e., a molecular oxygen-containing gas stream is supplied into the converting zone as described earlier, in an effort to remove and/or alleviate the poisoning and at least partly restore the performance of the converting catalyst. Alternatively, after the stoppage of the hydrogenation interval, the reactor is placed in an interruption interval, during which both the feed mixture and the molecular-oxygen-containing gas stream are not fed into the converting zone. After the interruption interval, an oxidation interval starts, in which both the feed mixture and the molecular-oxygen-containing gas stream are fed into the converting zone. An interruption interval between the hydrogenation interval and the oxidation interval can be beneficial where the converting reactor experienced a temperature excursion resulting in reactor trip.

Any suitable catalyst capable of converting the hydrogenation of an alkyne to form an olefin can be used as the converting catalyst in the processes of this disclosure. A converting catalyst can comprise a hydrogenation metal such as Fe, Co, Ni, Ru, Rh, Pd, Ag, Re, Os, Ir, Pt, and mixtures and combinations thereof. A preferred converting catalyst comprises Pd as a hydrogenation metal. Another preferred converting catalyst comprises Ni as a hydrogenation metal. A converting catalyst can comprise a support material for the hydrogenation metal. Such support can include, e.g., alumina, silica, zirconia, titania, thoria, alkaline earth oxides, rare earth oxides, and mixtures, compounds, and composites of two or more thereof. Such support can include naturally occurring materials such as clay, and/or synthetic materials. Examples of commercial converting catalysts useful for, e.g., acetylene conversion and/or MAPD conversion include, e.g., PRICAT™ PD 308 and 408 available from Johnson Matthey; FE E-DE2-4, FE E-DE2-5, FE-E-DC3, and FE E-RG series available from Chevron Phillips Chemical; Olemax® 200 series from Clariant; and LD-200 series from Axens.

In an alkyne converter, a load of converting catalyst is typically expected to sustain a normal run (i.e., an operation cycle, or a production campaign) starting from the startup of the production after a batch of the converting catalyst is loaded into the converter, during which its performance gradually decreases due to accumulation of coke, heavy hydrocarbons, and various poisons, until the end of the run when the operation of the converting reactor cannot be maintained in the designed operation envelope, at which time the reactor is shut down, the load of converting catalyst may be regenerated in-situ in the converting reactor, or unloaded from the reactor and optionally regenerated ex-situ. The in-situ regenerated converting catalyst can be utilized, or a new load of fresh and/or regenerated converting catalyst can be loaded into the reactor, thereafter to begin a new operation cycle. The processes of this disclosure can be particularly advantageously implemented after the converting catalyst has passed 50% (or 60%, or 70%, or 75%, or 80%, or 85%, or 90%, or 95%) of a normal run of the process by implementing an oxidation interval, whereby the partially contaminated and/or poisoned converting catalyst is at least partly restored or regenerated by contacting with molecular oxygen as described earlier. The processes of this disclosure can be particularly advantageously implemented during a beginning phase of an operation cycle when the converting catalyst is highly active and more prone to poisoning, particularly if the feed mixture comprises one or more catalyst poison(s) at appreciable level(s), to preserve the high initial catalyst activity for a prolonged period of time and maintain or prolong the service life of the converting catalyst. By implementing the oxidation interval once or repeatedly during the later stage of an operation cycle, regardless of whether an unexpected decrease of the performance of the converting catalyst has been detected, one can prolong the service life of the converting catalyst and/or achieve higher productivity of the converting reactor.

Certain contaminants in the feed mixture, e.g., arsenic, nitrogen-containing compounds, phosphorous-containing compounds, mercury, and the like, if at exceeding levels, can cause acute poisoning of the converting catalyst result in fast deactivation. When a feed mixture comprising such poisons at high concentrations is fed into the converting zone, it is highly advantageous to complement a process of this disclosure by also supplying a molecular-oxygen-containing gas stream into the converting zone. For example, if the feed mixture comprises arsenic at a concentration of ≥2 ppb (e.g., ≥3 ppb, ≥4 ppb, ≥5 ppb, ≥6 ppb, ≥7 ppb, ≥8 ppb) by mole, expressed as the mole concentration of $AsH_3$ on the basis of the total moles in the feed mixture, it would be highly advantageous to implement the oxidation interval. Without intending to be bound by a particular theory, it is believed that, if an oxygenation interval is not implemented, the following reactions can occur on the surface of the converting catalyst:

$$2AsH_3 + 3Pd \rightarrow Pd_3As_2 + 3H_2 \tag{R-1}$$

The effect of reaction (R-1) above is the loss of active catalytic Pd sites on the surface of the converting catalyst, manifested as catalyst poisoning. By supplying molecular oxygen into the converting zone, on contacting the converting catalyst and partly catalyzed by the converting catalyst, the following reactions may occur:

$$Pd_3As_2 + 3O_2 \rightarrow 3PdO + As_2O_3 \tag{R-2}$$

$$PdO + H_2 \rightarrow Pd + H_2O \tag{R-3}$$

$$2AsH_3 + 3O_2 \rightarrow As_2O_3 + 3H_2O \tag{R-4}$$

The effect of reactions (R-2), (R-3), and (R-4) above is the regeneration of an arsenic-poisoned catalyst site, and prevention of $AsH_3$ present in the feed mixture from further poisoning active Pd sites on the converting catalyst during the oxidation interval. While the above reactions use a Pd-containing converting catalyst as an example for illustration, one skilled in the art that other hydrogenation metal-containing converting catalyst can be benefited from the oxidation interval likewise.

The oxidation interval and the hydrogenation interval can be implemented as the same, similar, or different inlet temperatures. Thus, where a hydrogenation interval is carried out at a first inlet temperature of $T(1)°$ C., and an oxidation interval implemented after the hydrogenation interval is carried out at a second inlet temperature of $T(2)°$ C., the following can be satisfied: $0 \leq T(1)-T(2) \leq 12$, preferably $1 \leq T(1)-T(2) \leq 10$, preferably $1 \leq T(1)-T(2) \leq 8$, preferably $1 \leq T(1)-T(2) \leq 6$, preferably $1 \leq T(1)-T(2) \leq 5$, preferably $1 \leq T(1)-T(2) \leq 4$, preferably $1 \leq T(1)-T(2) \leq 3$.

In certain embodiments, after an oxidation interval following a first hydrogenation interval, one can start a second hydrogenation interval and supply the feed mixture into the converting zone through the feed inlet and contacting the feed mixture with the converting catalyst under converting conditions in the converting zone without supplying the molecular-oxygen-containing-gas stream into the converting zone. Desirably, at the beginning of the second hydrogenation interval, the converting catalyst exhibits a higher activity than at the end of the first hydrogenation interval due to the regeneration effect of the oxidation interval. Thus, in certain embodiments, at the end of the first hydrogenation interval, the feed mixture at the feed inlet has a temperature of $Ta°$ C. to maintain a threshold concentration of the alkyne in the first converted effluent; at the beginning of the second hydrogenation interval, the feed mixture at the feed inlet has a temperature of $Tb°$ C. to maintain the threshold concentration of the alkyne in the third converted effluent; and $Ta-Tb \geq 1$; preferably $Ta-Tb \geq 2$; preferably $Ta-Tb \geq 3$; preferably $Ta-Tb \geq 4$; preferably $Ta-Tb \geq 5$; preferably $Ta-Tb \geq 6$; preferably $Ta-Tb \geq 7$; preferably $Ta-Tb \geq 8$; preferably $Ta-Tb \geq 9$; preferably $Ta-Tb \geq 10$. One can implement a long oxidation interval and/or a high molecular oxygen concentration in the total feed mixture fed into the converting zone to effect a large reduction of inlet temperature after a single oxidation interval. One can also choose to implement multiple short oxidation intervals and/or a low molecular oxygen concentration in the total feed mixture fed into the converting zone to effect a moderate reduction of inlet temperature after each oxidation interval, but a large cumulative reduction of inlet temperature after the completion of multiple oxidation intervals separated by hydrogenation interval(s).

Surprisingly, it has been observed that at the beginning of the second hydrogenation interval, the converting catalyst can exhibit a higher selectivity for converting the alkyne to the olefin than at the end of the first hydrogenation interval at the same inlet temperature.

The feed mixture supplied into the converting zone can consist essentially of C1-C3 hydrocarbons and molecular hydrogen, and the C1-C3 hydrocarbons comprise the alkyne to be converted and the olefin the alkyne is to be desirably converted into. The C1-C3 hydrocarbons can include, at various amounts, methane, ethane, ethylene, acetylene, propane, propylene, methylacetylene, and propadiene.

In one embodiment, the feed mixture comprises molecular hydrogen, methane, ethane, acetylene, ethylene, propane, propylene, methylacetylene, and propadiene and is essentially free of C4+ hydrocarbons, and the converting zone is located in a front-end acetylene converter. The feed mixture can be a stream comprising molecular hydrogen significantly above stoichiometric quantity, produced from an upstream separation column, e.g., a de-propanizer which is upstream of a de-methanizer. On contacting the converting catalyst, the following desirable reactions can preferentially occur:

$$Acetylene + H_2 \rightarrow Ethylene \tag{R-5}$$

$$Methylacetylene + H_2 \rightarrow Propylene \tag{R-6}$$

$$Propadiene + H_2 \rightarrow Propylene \tag{R-7}$$

And the following undesirable reactions may occur at various degrees:

$$Ethylene + H_2 \rightarrow Ethane \tag{R-8}$$

$$Propylene + H_2 \rightarrow Propane \tag{R-9}$$

$$2\, Acetylene + H_2 \rightarrow Butadiene \tag{R-10}$$

$$m\, Acetylene + n\, Butadiene + k\, H_2 \rightarrow Oligomeric\ Heavy\ Hydrocarbons \tag{R-11}$$

$$2\, Methylacetylene + H_2 \rightarrow 2,4\text{-Hexadiene} \tag{R-12}$$

$$x\, Methylacetylene + y\, 2,4\text{-Hexadiene} + z\, H_2 \rightarrow Oligomeric\ Heavy\ Hydrocarbons \tag{R-13}$$

It is highly desired that the converting catalyst is selective for reactions (R-5), (R-6), and (R-7), and reactions (R-8), (R-9), (R-10), (R-11), (R-12), and (R-13) are minimized. The oligomeric heavy hydrocarbons can accumulate on the converting catalyst, resulting in gradual loss of catalyst activity over time during the operation cycle.

In another embodiment, the feed mixture comprises molecular hydrogen, methane, ethane, acetylene, and ethylene, and is essentially free of C3+ hydrocarbons, and the converting zone is located in a front-end acetylene converter. The feed mixture can be a stream comprising molecular hydrogen significantly above stoichiometric quantity, produced from an upstream separation column, e.g., a de-ethanizer which is upstream of a de-methanizer. On contacting the converting catalyst, the following desirable reactions can preferentially occur:

$$Acetylene + H_2 \rightarrow Ethylene \tag{R-5}$$

And the following undesirable reactions may occur at various degrees:

$$Ethylene + H_2 \rightarrow Ethane \tag{R-8}$$

$$2\, Acetylene + H_2 \rightarrow Butadiene \tag{R-10}$$

$$m\, Acetylene + n\, Butadiene + k\, H_2 \rightarrow Oligomeric\ Heavy\ Hydrocarbons \tag{R-11}$$

It is highly desired that the converting catalyst is selective for reactions (R-5), and reactions (R-8), (R-10), and (R-11) are minimized.

In another embodiment, the feed mixture comprises molecular hydrogen, ethane, acetylene, and ethylene, and is essentially free of $CH_4$ and C3+ hydrocarbons, and the converting zone is located in a back-end acetylene converter. The feed mixture can be a stream produced by (Ia) providing a C2 hydrocarbon stream; and (Ib) supplying molecular hydrogen into the C2 hydrocarbon stream to form the feed mixture. The C2 hydrocarbon stream, essentially free of molecular hydrogen, can be produced from an upstream separation column, e.g., a de-ethanizer which is downstream of a de-methanizer. On contacting the converting catalyst, the following desirable reactions can preferentially occur:

$$\text{Acetylene} + H_2 \rightarrow \text{Ethylene} \quad \text{(R-5)}$$

And the following undesirable reactions may occur at various degrees:

$$\text{Ethylene} + H_2 \rightarrow \text{Ethane} \quad \text{(R-8)}$$

$$2\ \text{Acetylene} + H_2 \rightarrow \text{Butadiene} \quad \text{(R-10)}$$

$$m\ \text{Acetylene} + n\ \text{Butadiene} + k\ H_2 \rightarrow \text{Oligomeric Heavy Hydrocarbons} \quad \text{(R-11)}$$

It is highly desired that the converting catalyst is selective for reactions (R-5), and reactions (R-8), (R-10), and (R-11) are minimized. To that end, it is desirable that the molecular hydrogen supplied in step (Ib) above has a molar quantity substantially identical to the acetylene present in the C2 hydrocarbon stream.

In another embodiment, the feed mixture comprises molecular hydrogen, propane, methylacetylene, and propadiene, and is essentially free of C2- and C4+ hydrocarbons, and the converting zone is located in a MAPD converter. The feed mixture can be a stream produced by (Ic) providing a C3 hydrocarbon stream; and (Id) supplying molecular hydrogen into the C3 hydrocarbon stream to form the feed mixture. The C3 hydrocarbon stream, essentially free of molecular hydrogen, can be produced from an upstream separation column, e.g., a de-propanizer which is downstream of a de-ethanizer. On contacting the converting catalyst, the following desirable reactions can preferentially occur:

$$\text{Methylacetylene} + H_2 \rightarrow \text{Propylene} \quad \text{(R-6)}$$

$$\text{Propadiene} + H_2 \rightarrow \text{Propylene} \quad \text{(R-7)}$$

And the following undesirable reactions may occur at various degrees:

$$\text{Propylene} + H_2 \rightarrow \text{Propane} \quad \text{(R-9)}$$

$$2\ \text{Methylacetylene} + H_2 \rightarrow 2,4\text{-Hexadiene} \quad \text{(R-12)}$$

$$x\ \text{Methylacetylene} + y\ 2,4\text{-Hexadiene} + z\ H_2 \rightarrow \text{Oligomeric Heavy Hydrocarbons} \quad \text{(R-13)}$$

It is highly desired that the converting catalyst is selective for reactions (R-5), and reactions (R-9), (R-12), and (R-13) are minimized. To that end, it is desirable that the molecular hydrogen supplied in step (Id) above has a molar quantity substantially identical to the MAPD present in the C3 hydrocarbon stream.

During the alkyne conversion processes, heavy hydrocarbons can be formed and accumulate on the converting catalyst, causing gradual loss of the catalyst activity, presumably due to, among others, reactions (R-10), (R-11), (R-12), and (R-13). Overtime, coke can form on the converting catalyst from such heavy hydrocarbons. It has been found that, surprisingly, the processes of this disclosure including an oxidation interval in which a molecular-oxygen-containing gas stream is fed into the converting zone along with the feed mixture can be effectively employed to prevent the formation of heavy hydrocarbons and coke on the converting catalyst, or to reduce the amount of heavy hydrocarbons and coke already formed and existing on the converting catalyst. Without intending to be bound by a particular theory, it is believed that the converting catalyst catalyzes/promotes the oxidation of such heavy hydrocarbon and coke on its surface. It has been surprisingly found that, after an oxidation interval, a converting catalyst previously contaminated by heavy hydrocarbons/coke exhibited higher selectivity for reaction (R-5) than for reaction (R-8), contrary to previous reports on effects of exposure to oxygen to the acetylene converting catalyst in a FEAC.

Various embodiments of the second and third aspects of this disclosure are apparent in the light of the earlier description.

DESCRIPTION OF THE FIGURE

The FIGURE schematically illustrates a portion of the process flow of the recover section of an olefins production plant in which various embodiments of the processes of this disclosure may be implemented. For the simplicity of illustration and description, certain heat exchangers, vessels, conduits, reflux streams, recycle streams, valves, meters, sensors, pumps, instruments, and the like, are not shown. As shown in the FIGURE, a compressed process gas stream 103, consisting essentially of C1-C5 hydrocarbons and molecular hydrogen, is separated to recover a C5 hydrocarbon stream 113, a C4 hydrocarbon stream 111, a propane stream 181, a propylene stream 179, an ethane stream 163, an ethylene stream 161, and a tail gas stream 141 comprising methane and molecular hydrogen. Stream 103 may be a fraction produced from, e.g., a primary fractionator (not shown) receiving a quenched/cooled effluent produced from a steam cracker (not shown), preferably subjected to one or more stages of compression (not shown) to an elevated pressure, caustic wash (not shown) to remove sour gas such as $H_2S$ and $CO_2$ and then drying (not shown) to remove water therefrom.

The compressed process gas stream 103 is fed into a de-propanizer 105 operating under suitable conditions to produce an overhead vapor stream 115 rich in C3- hydrocarbons and molecular hydrogen and a bottoms liquid stream 107 rich in C4-C5 hydrocarbons. Stream 107 is then fed into column 109 operating under suitable conditions to produce an overhead vapor stream 111 rich in C4 hydrocarbons and a bottoms liquid stream 113 rich in C5 hydrocarbons. Stream 111 may be further separated (not shown) to produce various product streams, e.g., a butenes stream, a butanes stream, and the like. Stream 113 may be further separated (not shown) to produce various product streams.

Stream 115, rich in C3- hydrocarbons and molecular hydrogen, may comprise various proportions of desired light olefins ethylene and propylene and molecular hydrogen. Stream 115 can also comprise methane, ethane, and propane at various quantities. While a steam cracker can be optimized to produce much more ethylene and propylene than acetylene, methylacetylene, and propadiene, stream 115 invariably comprises acetylene, methylacetylene, and propadiene at various quantities. Without abatement of acetylene in the recovery section, the ethylene product stream 161 recovered from stream 115 can comprise acetylene at a concentration exceeding the specification required for down-stream use of stream 161, e.g., for polymerization to make various grades of polyethylene and other polymers. Without abatement of MAPD in the recovery section, the propylene product stream 179 recovered from stream 115 can comprise MAPD at concentrations exceeding the specification required for down-stream use of stream 179, e.g., for polymerization to make various grades of polypropylene and other polymers.

As shown in the FIGURE, stream 115 is then compressed by a compressor 117 to form a stream 118 at a higher pressure desirably in vapor phase, which is then fed into a front-end acetylene converter 121 having a converting zone in which a converting catalyst bed 123 is installed. The converting catalyst in bed 123 can comprise a hydrogenation metal (e.g., Fe, Co, Ni, Ru, Rh, Pd, Re, Os, Ir, Pt, preferably Pd) and a support (e.g., alumina, silica, zirconia, titania, clay, and mixtures and combinations thereof). Upon contacting the converting catalyst bed 123, a portion, preferably a majority, of the acetylene in the feed mixture of stream 118 is converted, via hydrogenation by the molecular hydrogen in stream 118, to ethylene; a portion, preferably a majority, of the methylacetylene in the feed mixture stream 118 is converted, via hydrogenation, to propylene; and a portion, preferably a majority, of the propadiene in the feed mixture stream 118 is converted, via hydrogenation, to propylene. The converted effluent 125 desirably comprises acetylene, methylacetylene, and propadiene at lower levels compared to stream 118.

In addition to the desired selective hydrogenation of the alkynes and dienes into olefins in the acetylene converter 121, certain undesirable side reactions may occur, e.g., hydrogenation of the olefins to saturated hydrocarbons, polymerization of the olefins, alkynes, and/or dienes to form heavy hydrocarbons such as oligomers, and the formation of coke. Modern alkyne conversion catalysts can be highly selective for the hydrogenation of alkynes and dienes to the desired olefin molecules. Nonetheless, such side reactions can occur to various degrees under various reaction conditions. As a result, over time, heavy hydrocarbons and coke can accumulate over the converting catalyst, resulting in reduced activity and/or selectivity of the converting catalyst. Furthermore, depending on the hydrocarbon feed to the upstream steam cracker, streams 103, 115, and 118 may comprise various catalyst poisons such as nitrogen-containing compounds, phosphorous-containing compounds, arsenic-containing compounds, oxygen-containing compounds, sulfur-containing compounds, halide-containing compounds, alkali metal elements, and the like. Exposure to the catalyst poisons over time can cause the reduction of catalyst activity and selectivity.

We have surprisingly found that by supplying a molecular oxygen-containing gas stream 119 together with the feed mixture stream 118 into the acetylene converter 121, the performance of the converting catalyst bed 123 can be enhanced without interrupting the operation of the converter 121. The molecular oxygen-containing gas stream can be, e.g., (a) pure $O_2$; (b) pure $O_3$; (c) air; (d) a mixture of $O_2$ with one or more inert gas (e.g., $N_2$, $CH_4$, $C_2H_6$, $C_3H_6$, $CO_2$, $H_2O$, He, Ne, Ar, Kr, and the like, and mixtures thereof); and (e) a mixture of two or more of (a), (b), (c), and (d). Preferably stream 119 is compressed air, or a diluted air comprising one or more inert gas such as $N_2$, He, Ne, Ar, Kr, $H_2O$, and the like. Preferably stream is an $O_2/N_2$ mixture stream. Preferably stream 119 comprises molecular oxygen at a concentration from 5% to 20% by mole, based on the total moles in the molecular oxygen-containing gas stream 119. While stream 119 can be directly fed into converter 121, preferably stream 119 is first mixed with stream 118 to form a molecular-oxygen-containing feed mixture stream 120, which is then fed into the converter 121 via the feed inlet. Preferably, the molecular oxygen molecules are substantially homogeneously distributed in the $O_2$-containing feed mixture when entering the converter 121. The quantity of the stream 119 fed into the converter 121 can vary depending on, e.g., the specification of $CO_2$ required for the final ethylene product stream 161, the degree of performance enhancement for the converting catalyst, and the like. Preferably, the quantity of the molecular oxygen-containing gas stream 119 fed into the converter 121 corresponds to a molecular oxygen concentration in a range from 0.25 to 100 ppm (preferably from 0.5 to 90 ppm, preferably from 0.5 to 80 ppm, preferably from 0.5 to 70 ppm, preferably from 0.5 to 60 ppm, preferably from 0.5 to 50 ppm, preferably from 0.5 to 40 ppm, preferably from 0.5 to 30 ppm, preferably from 0.5 to 20 ppm, preferably from 0.75 to 10 ppm, preferably from 1 to 8 ppm, preferably from 1 to 6 ppm, preferably from 1 to 5 ppm, preferably from 1 to 4 ppm) by mole, on the basis of the total moles of molecules in the feed mixture.

Without intending to be bound by a particular theory, it is believed that the oxygen molecules in stream 119, upon entering the converter 121, on contacting the converting catalyst bed 123, can preferentially oxidize molecules in its vicinity present on the converting catalyst. It is believed that the converting catalyst catalyzes, in addition to the preferential hydrogenation of alkyne(s) and diene(s) to olefin(s), oxidation of coke, heavy hydrocarbons, light hydrocarbons, and various poison species present on converting catalyst, by the oxygen molecules supplied through stream 119. As a result, existing coke, heavy hydrocarbons, and certain temporary or semi-permanent poison species, if any, adhered to the converting catalyst, can be removed, either from the converting catalyst completely, or at least from the active sites of the converting catalyst, resulting in increased quantity of active catalyst sites, and hence enhanced catalyst performance or preservation of the catalyst performance for a longer period. While the oxidation reactions occur, the desirable selective hydrogenation of the alkyne and/or selective hydrogenation of diene(s) to form the olefin can continue simultaneously without interruption. In effect, by intentionally feeding molecular oxygen into the alkyne converter in the processes of this disclosure, one can surprisingly achieve online regeneration of the converting catalyst without interrupting the normal operation of the converter.

In one embodiment, the molecular oxygen-containing gas stream 119 is not fed into the converter 121 in a hydrogenation interval during which only the feed mixture stream 118 is fed into the converter 121 and allowed to contact the converting catalyst bed 123 to produce a first converted effluent 125. As the hydrogenation interval progresses, one or more of coke, heavy hydrocarbons, and catalyst poison may accumulate on the converting catalyst, resulting in the gradual reduction of its activity and/or selectivity. To achieve a desirable level of acetylene concentration in stream 125, the inlet temperature can be increased. When the inlet temperature reaches a predetermined threshold, e.g., the middle of the operation envelope, one can end the hydrogenation interval and start an oxidation interval by feeding the molecular oxygen-containing gas stream 119 while maintaining the flow of stream 118, which mixes with stream 118 to form stream 120, which is then fed into the converter 121 via the feed mixture inlet. During the oxidation interval, the molecular oxygen supplied in stream 119 and the feed mixture in stream 118 contact the converting catalyst bed 123, where the species adsorbed on the converting catalyst (e.g., coke, heavy hydrocarbons, and poison species) are oxidized, removed, or transferred away from the active sites of the converting catalyst, resulting in an enhanced converting catalyst. The oxidation interval can vary in length from, e.g., several minutes to multiple weeks, depending on the severity the contamination of the converting catalyst at the end of the hydrogenation interval, and the degree of performance enhancement. After the oxidation interval, when the converting catalyst has been regenerated to a desired level of performance, one can shut down stream 119 while maintaining stream 118, effectively starting a second hydrogenation interval.

In certain specific embodiments, one can monitor the performance of the converting catalyst during a hydrogenation interval, and stop the hydrogenation interval when an unexpected decrease of performance of the converting catalyst is observed. Examples of unexpected decrease of performance include but are not limited to (a) an increase of inlet temperature of ≥5° C. within 24 hours while maintaining substantially constant alkyne concentration in the first converted effluent; and (b) a temperature excursion resulting in reactor trip. Afterwards, one can immediately start the oxidation interval to enhance the converting catalyst. Alternatively, one can wait for an interruption interval after the termination of the hydrogenation interval (e.g., shutting down the alkyne reactor) before starting the oxidation interval in certain situations, e.g., where a temperature excursion occurs and the alkyne converter has to cool down first.

In another embodiment, a continuous molecular oxygen-containing gas stream 119 can be fed into the converter 121 along with the feed mixture stream 118 for a prolonged period of time. In such embodiment, the oxygen molecules supplied from stream 119 can prevent or reduce the formation or accumulation of coke, heavy hydrocarbons and poisons on the converting catalyst, resulting in the preservation of a high catalyst performance for a longer period compared to the prior art process where no molecular oxygen is intentionally supplied into the converter 121, hence a lower required rate of increasing the inlet temperature over time, and a longer run length of a batch of the converting catalyst. Such an embodiment can be particularly advantageous where the feed mixture stream 118 is known to comprise a catalyst poison (e.g., $AsH_3$) at an elevated concentration. As described above, by controlling the quantity (e.g., flow rate) of stream 119, and the concentration of molecular oxygen in stream 119, one can achieve desirable levels of acetylene and $CO_2$ simultaneously in the converted effluent 125 exiting the converter 121.

On contacting the feed mixture with the converting catalyst bed 123, during the hydrogenation interval or the oxidation interval, the following desirable reactions can preferentially occur in the converter 121:

Acetylene+$H_2$→Ethylene (R-5)

Methylacetylene+$H_2$→Propylene (R-6)

Propadiene+$H_2$→Propylene (R-7)

As such, the converted effluent stream 125 exiting the converter 121 desirably comprises acetylene, methylacetylene, and propadiene at concentrations lower than in stream 118. In addition, the following undesirable reactions may occur at various degrees during the hydrogenation interval:

Ethylene+$H_2$→Ethane (R-8)

Propylene+$H_2$→Propane (R-9)

2 Acetylene+$H_2$→Butadiene (R-10)

$m$ Acetylene+$n$ Butadiene+$k$ $H_2$→Oligomeric Heavy Hydrocarbons (R-11)

2 Methylacetylene+$H_2$→2,4-Hexadiene (R-12)

$x$ Methylacetylene+$y$ 2,4-Hexadiene+$z$ $H_2$→Oligomeric Heavy Hydrocarbons (R-13)

It is highly desired that the converting catalyst is selective for reactions (R-5), (R-6), and (R-7) and reactions (R-8), (R-9), (R-10), (R-11), (R-12), and (R-13) are minimized. The oligomeric heavy hydrocarbons can accumulate on the converting catalyst, resulting in gradual loss of catalyst activity over time during the hydrogenation cycle.

During the oxidation interval, stream 125 may comprise $CO_2$ and $H_2O$ at concentrations higher than stream 118. By controlling the flow rate of stream 119 and $O_2$ concentration in stream 119, one can effectively control the $CO_2$ concentration in stream 125, such that the $CO_2$ concentration in the ethylene stream 161 does not exceed a predetermined specification level.

As shown in the FIGURE, stream 125 can be compressed by one or more compressors 127 to form a stream 129 at a higher pressure, which can be preferably dried in a drier 131. Driver 131 can comprise a bed of water adsorbent therein. The dried effluent 133 exiting drier 131, comprising C1-C3 hydrocarbons and molecular hydrogen, can be then cooled by a heat exchanger (e.g., in a cold box of an olefins recovery section of an olefins production plant) to obtain a gas-liquid mixture stream 137, which is then fed into a demethanizer column 139. An overhead vapor stream 141, rich in methane and molecular hydrogen, and a bottoms liquid stream 143, rich in C2-C3 hydrocarbons, are produced from column 139. Stream 141 can be further separated (not shown) to obtain a molecular hydrogen stream, an optional $CH_4$ stream, and an optional $H_2/CH_4$ mixture stream. Various streams may be recycled to column 139 (not shown). A portion of the molecular hydrogen stream can be supplied the back-end acetylene converter 153 and the MAPD converter 171 (described below).

Stream 143 can be fed into a de-ethanizer column 145, from which an overhead vapor stream 147 rich in C2 hydrocarbons and a bottoms liquid stream 165 rich in C3 hydrocarbons are obtained. Stream 147 may consist essentially of ethylene and ethane and optionally acetylene as a contaminant. Where stream 147 comprises acetylene at a concentration sufficiently high to result in the downstream ethylene product stream 161 comprising acetylene above the specification required, one can further abate the acetylene in stream 147 in a trim converter 153 by selectively hydrogenating acetylene to ethylene. Because stream 147 is essentially free of molecular hydrogen, a molecular hydrogen stream 149 is combined with stream 147 to form a feed mixture stream 150, which is then fed into trim converter 153. Trim converter 153 is a back-end converter in that stream 147 produced from de-ethanizer 145 is essentially free of molecular hydrogen. A converting catalyst bed 155 is installed in converter 153. The converting catalyst in bed 155 can be the same as or different from the converting catalyst in bed 123 in the front-end converter 121. Preferably, a greater majority of acetylene present in stream 118 has already been selectively converted into ethylene in converter 121, leaving only a small quantity, if any, of acetylene remaining in stream 147 in need of additional abatement in converter 153. In such embodiment the trim converter 153 can advantageously have a capacity much smaller than converter 121. Preferably, the molar amount of molecular hydrogen in stream 149 fed into trim converter 153 is approximately equal to the molar amount of acetylene present in stream 147, such that substantially all of the acetylene in stream 147 and all molecular hydrogen in stream 149 are consumed in trim converter 153 in the selective hydrogenation of acetylene, leaving negligible amount of acetylene in the converted effluent stream 157 exiting trim converter 153, and little, if any, residual molecular hydrogen that may hydrogenate ethylene to ethane in trim converter 153.

Similar to the operation of the front-end acetylene converter 121 as described above, as shown in the FIGURE, a molecular oxygen-containing gas stream 151 can be fed into feed mixture stream 150 to form a molecular-oxygen-containing feed mixture stream 152, which is then fed into trim converter 153. The composition of stream 151 can the same as or different from that of stream 119. On contacting the converting catalyst bed 155, the molecular oxygen thus introduced into trim converter 153 can function in the same manner as in converter 121 as described above to preserve, enhance, or regenerate the converting catalyst. Similarly, stream 151 can be fed into trim converter 153 only intermittently in one or more oxidation intervals with various durations following hydrogenation intervals with various durations, or continuously into the trim converter 153 for a prolonged oxidation interval.

The converted effluent 157 exiting the trim converter 153, desirably essentially free of acetylene, can be then fed into a C2 splitter column 159, from which an overhead stream 161 rich in ethylene and a bottoms stream 163 rich in ethane are produced. Desirably, stream 161 comprises acetylene and $CO_2$ at below specification levels. Stream 163 can be recycled to the steam cracker (not shown) to produce more olefins.

Stream 165 exiting de-ethanizer 145, rich in C3 hydrocarbons, may comprise, in addition to propane and propylene, various amounts of MAPD. As described above, a portion, preferably a majority, of MAPD present in stream 118 have been converted into propylene in the front-end acetylene converter 121. Nonetheless, a non-negligible portion of MAPD may make their way into stream 165, which, if not further abated, can cause their concentration in the downstream propylene product stream 179 to exceed a threshold level required by its specification. In such embodiment, it is highly desirable to further abate the MAPD in a MAPD converter 171 by selectively hydrogenating the MAPD into propylene. Because stream 165 is essentially free of molecular hydrogen, a molecular hydrogen stream 166 is combined with stream 165 to form a feed mixture stream 167, which is then fed into the MAPD converter 171. The MAPD converter 171 is a back-end converter in that stream 165 produced from de-ethanizer 145 is essentially free of molecular hydrogen. A converting catalyst bed 173 is installed in the MAPD converter 171. The converting catalyst in bed 173 can be the same as or different from (i) the converting catalyst in bed 123 in the front-end converter 121 and/or (ii) the converting catalyst in bed 155 in the back-end converter 153. Preferably, a greater majority of MAPD present in stream 118 has already been selectively converted into propylene in converter 121, leaving only a small quantity, if any, of MAPD remaining in stream 165 in need of additional abatement in the MAPD converter 171. In such embodiment the MAPD converter 171 can advantageously have a capacity much smaller than converter 121. Preferably, the molar amount of molecular hydrogen in stream 155 fed into the MAPD converter 171 is approximately equal to the molar amount of MAPD present in stream 165, such that substantially all of the MAPD in stream 165 and all molecular hydrogen in stream 166 are consumed in the MAPD converter 171 in the selective hydrogenation of MAPD, leaving negligible amount of MAPD in the converted effluent stream 175 exiting the MAPD converter 171, and little, if any, residual molecular hydrogen that may hydrogenate propylene to propane in the MAPD converter 171.

The converted effluent 175 exiting the MAPD converter 171, desirably essentially free of MAPD, can be then fed into a C3 splitter column 177, from which an overhead stream 179 rich in propylene and a bottoms stream 181 rich in propane are produced. Desirably, stream 181 comprises MAPD at below specification levels. Stream 179 can be recycled to the steam cracker (not shown) to produce more olefins.

The FIGURE only shows certain specific configurations and operation of a portion of the product recovery section of an olefins production plant. Other configures and operations are possible, in which the operation of the alkyne converter (s) can vary accordingly. For example, in an alternative embodiment, the compressed process gas stream 103 can be fed into a de-methanizer instead of a de-propanizer as shown in the FIGURE. In such embodiment the bottoms liquid stream from the de-methanizer, rich in C2+ hydrocarbons and depleted in $CH_4$ and $H_2$, can be fed into a de-ethanizer to produce an overhead stream rich in C2 hydrocarbons and a bottoms stream rich in C3+ hydrocarbons. The overhead stream rich in C2 hydrocarbons can be then fed into a back-end acetylene converter along with a molecular hydrogen stream and an optional molecular oxygen-containing gas stream to abate the acetylene contained therein. The back-end acetylene converter can be larger than the trim converter 153 in the FIGURE as described above, and operated in ways similar to converter 153. The bottoms stream from the de-ethanizer rich in C3+ hydrocarbons can be fed into a de-propanizer to produce an overhead stream rich in C3 hydrocarbons and a bottoms stream rich in C4+ hydrocarbons. The overhead stream can then be fed into a MAPD converter along with a molecular hydrogen stream and an optional molecular oxygen-containing gas stream to abate the MAPD contained therein. The MAPD converter can be operated in ways similar to the MAPD converter 171 shown in the FIGURE. The bottoms stream rich in C4+ hydrocarbons can be separated in a de-butanizer to produce an overhead stream rich in C4 hydrocarbons and a bottoms stream rich in C5 hydrocarbons.

In another alternative embodiment, the compressed process gas stream 103 can be fed into a de-ethanizer instead of a de-propanizer as shown in the FIGURE. In such embodiment the overheads stream from the de-ethanizer, rich in C1-C2 hydrocarbons and $H_2$, can be fed into a front-end acetylene converter along with an optional molecular oxygen-containing gas stream to abate the acetylene contained therein. Such front-end acetylene converter can be structured and operated in ways similar to the converter 121 shown in the FIGURE and described in detail above. The effluent from the front-end acetylene converter can then be further separated in a de-methanizer to obtain a C2-rich stream and a tail gas stream comprising $CH_4$ and hydrogen. The C2-rich stream, upon optional treatment in a back-end converter to abate any residual acetylene therein in ways similar to converter 153 in the FIGURE, can be separated in a C2 splitter column to produce an ethylene product stream and an ethane stream, the latter of which can be recycled to a steam cracker. The bottoms stream from the de-ethanizer rich in C3+ hydrocarbons can be fed into a de-propanizer to produce an overhead stream rich in C3 hydrocarbons and a bottoms stream rich in C4+ hydrocarbons. The overhead stream can then be fed into a MAPD converter along with a molecular hydrogen stream and an optional molecular oxygen-containing gas stream to abate the MAPD contained therein. The MAPD converter can be operated in ways similar to the MAPD converter 171 shown in the FIGURE. The bottoms stream rich in C4+ hydrocarbons can be separated in a de-butanizer to produce an overhead stream rich in C4 hydrocarbons and a bottoms stream rich in C5 hydrocarbons.

This disclosure is further illustrated by the following non-limiting examples.

EXAMPLES

Example 1

A first front-end acetylene converter ("FEAC") comprising a fixed bed of Pd-containing converting catalyst was monitored, studied, and tested. In an initial hydrogenation interval, a hydrocarbon feed mixture comprising $CH_4$, ethane, ethylene, propane, propylene, molecular hydrogen, ≤2000 ppm by mole of CO, ≤5000 ppm by mole of acetylene, ≤50 mole ppb of molecular oxygen, and from 1 ppb to 10 ppb by weight of $AsH_3$ was fed through a feed inlet into the first FEAC. A converted effluent exiting the converter comprised acetylene at a lower concentration than the feed mixture. The inlet temperature was adjusted to maintain a predetermined, substantially stable, desired acetylene concentration in the converted effluent in this Example 1.

During a first period of operation (a hydrogenation interval) of about 30 days, the feed mixture comprised $AsH_3$ at a concentration of about 4 to 5 ppb by weight, and the inlet temperature was maintained at above 200° F. (93.3° C.), with an average of about 212° F. (100° C.), which resulted in the acetylene concentration in the converted effluent at the substantially stable, desired level. During a second period of operation (a hydrogenation interval) of about 45 days after the first period, the feed mixture comprised $AsH_3$ at a reduced concentration of about 1 ppb by weight, a reduced concentration of CO at about <1000 ppm by mole, and the inlet temperature was reduced and maintained at about 180° F. (82.2° C.) to achieve an acetylene concentration in the converted effluent at the substantially stable, desired level. Afterwards, in a third period of operation (a hydrogenation interval) of about 30 days, the feed mixture resumed to comprise $AsH_3$ at a concentration of about 4 to 5 ppb by weight, a concentration of CO at 1500 to 2000 ppm by mole, and the inlet temperature was increased to and maintained at above 200° F. (93.3° C.), with an average of about 213° F. (100.6° C.), which resulted in the acetylene concentration in the converted effluent at the substantially stable, desired level, similar to the first period of operation. After the third period of operation, in a fourth period of operation (a hydrogenation interval) of about 25 days, the feed mixture comprised $AsH_3$ at an increased concentration of about 6-8 ppb by weight, with the concentration of CO remaining in the 1500 to 2000 ppm by mole range, and to maintain the acetylene concentration in the converted effluent at the substantially stable, desired level, the inlet temperature was gradually increased from about 210° F. (98.9° C.) to about 255° F. (124° C.). Thus, from the operations in the first, second, third, and fourth periods, the impact of $AsH_3$ concentration in the hydrocarbon feed mixture was clearly observed: at ppb levels, the higher the $AsH_3$ in the hydrocarbon feed mixture, the higher the inlet temperature is required to maintain the same level of acetylene conversion, indicating that $AsH_3$ is a potent catalyst poison to the Pd-containing converting catalyst. Without intending to be bound by a particular theory, it is believed that the following reaction at the active Pd metal sites may have occurred, resulting in the loss of a certain amount of active sites and the corresponding loss of catalyst activity:

$$2AsH_3+3Pd \rightarrow Pd_3As_2+3H_2 \tag{R-1}$$

At the end of the fourth period, a fifth period of operation, which is an oxidation interval, was initiated. At the beginning of this period, a stream of compressed air was injected into the hydrocarbon feed mixture used in the third period to form a molecular-oxygen-containing feed mixture comprising $O_2$ at a concentration of about 35 ppm by mole (assuming no consumption of $O_2$ before the molecular-oxygen-containing feed mixture entered the first FEAC). The molecular-oxygen-containing feed mixture is then fed into the first FEAC to contact the converting catalyst. The fifth period of operation lasted for about 10 minutes, at the end of which the stream of compressed air was shut off and a sixth period of operation, a hydrogenation interval, began. During the sixth period, the hydrocarbon feed mixture comprised $AsH_3$ of about 6-8 ppb by weight, the same level as in the fourth period. In the beginning of the sixth period, the inlet temperature was sharply reduced to only about 210° F. (98.9° C.), about 40-45° F. (22-25° C.) lower than at the end of the fourth period, to achieve the acetylene concentration in the converted effluent at the substantially stable, desired level. This clearly demonstrated that air injection during the fifth period, even at a very low injection rate and for a very short period of time, resulted in substantial enhancement of the performance of the converting catalyst from the end of the fourth period. Without intending to be bound by a particular theory, it is believed the following reactions may have occurred during the oxidation interval, resulting in regenerating. As-poisoned Pd catalyst sites and prevention of further. As poisoning during the oxidation interval:

$$Pd_3As_2+3O_2 \rightarrow 3PdO+As_2O_3 \tag{R-2}$$

$$PdO+H_2 \rightarrow Pd+H_2O \tag{R-3}$$

$$2AsH_3+3O_2 \rightarrow As_2O_3+3H_2O \tag{R-4}$$

The $As_2O_3$ formed in the above reaction (R-2) at least partly migrates away from the Pd phase, exposing regenerated, active Pd catalytic phase, resulting in enhanced activity in catalyzing the hydrogenation of the alkynes and diene(s), hence a lower required inlet temperature to achieve the acetylene concentration in the converted effluent at the substantially stable, desired level.

The sixth period lasted for about 15 days, during which the inlet temperature was gradually increased from about 210° F. (98.9° C.) to about 255° F. (124° C.), similar to the third period, demonstrating the lasting regeneration effect of the converting catalyst in the fourth period, and indicating, during the sixth period, the occurrence of reaction (R-1) and gradual poisoning of the Pd-containing converting catalyst by the high concentration of $AsH_3$ in the hydrocarbon feed mixture.

At the end of the sixth period, a seventh period, which is an oxidation interval, was initiated. The seventh period was a repeat of the fifth period Immediately afterwards, an eighth period, a hydrogenation interval, was initiated using the same hydrocarbon feed mixture of the fifth period. Similar to the sixth period, during the eighth period, the inlet temperature was gradually increased from about 210° F. (98.9° C.) to about 255° F. (124° C.) in about 12 days, demonstrating the pronounced effect of regeneration of the converting catalyst in the sixth period, and indicating, during the eighth period, the occurrence of reaction (R-1) and gradual poisoning of the Pd-containing converting catalyst by the high concentration of $AsH_3$ in the hydrocarbon feed mixture.

Thereafter, additional five alternating oxidation intervals (i.e., the ninth, eleventh, thirteenth, and fifteenth periods) similar to the fifth and seventh periods and additional five hydrogenation intervals (i.e., the tenth, twelfth, fourteenth, and sixteenth periods) similar to the sixth and eighth periods were implemented with the first FEAC. It was consistently observed that, following each oxidation interval, in the beginning of each subsequent hydrogenation interval, the inlet temperature was reduced substantially due to a substantially improved performance of the converting catalyst, and as the hydrogenation intervals progressed, the inlet temperature was increased due to gradual poisoning of the converting catalyst by the $AsH_3$ in the hydrocarbon feed mixture at high concentration.

The tests in this Example 1 clearly demonstrated the poisoning effect of $AsH_3$ on a converting catalyst, particularly a Pd-containing converting catalyst, and the surprising and consistent regeneration effect of the poisoned converting catalyst by the introduction of molecular $O_2$ into the first FEAC, even at a low concentration thereof in the total feed supplied into the FEAC.

The presence of $CO_2$ was observed in the ethylene product stream produced from the converted effluent exiting the first FEAC following each introduction of the molecular-oxygen-containing gas stream into the first FEAC. However, the $CO_2$ concentrations were peaked at levels within required product specifications at generally below 5 ppm by mole in the ethylene product, based on the total moles of the ethylene product stream.

Conventionally, molecular $O_2$, if present in the feed to an alkyne converter, is considered as a catalyst poison for a variety of reasons. First, $O_2$ may oxidize the active metal such as Pd in the converting catalyst, turning it into an oxide which does not have the desired alkyne/diene hydrogenation catalytic effect, thereby reducing the activity of the catalyst. Because the operating temperature in the alkyne converter is relatively low, the oxidized active metal may not be reduced by the hydrocarbon and/or molecular hydrogen in the converter to the active metallic state. Second, $O_2$ was suspected of oxidizing the hydrocarbons in the feed, especially the majority species such as the olefins and alkanes, forming $CO_2$ and $H_2O$, potentially resulting in downstream olefin products, especially the ethylene product, comprising $CO_2$ exceeding the required specifications. Third, traditional regeneration of the converting catalyst is conducted in the presence of large quantity of molecular $O_2$, e.g., air, at elevated temperature, whereby the contaminants on the catalyst are oxidized and preferably removed. Introducing molecular $O_2$ at such large quantity into an operating alkyne converter while feeding the hydrocarbon mixture feed, is, however, impractical and dangerous, because the reactions between such large quantity of $O_2$ with the hydrocarbons and/or molecular hydrogen can easily result in temperature excursion and forced shutdown of the alkyne converter. Feeding molecular $O_2$ into an operating alkyne converter at a small quantity, as in the processes of this disclosure, on the other hand, was perceived to be insufficient to regenerate the converting catalyst because of the consumption of molecular oxygen molecules by the large amount of hydrocarbon and molecular hydrogen present in the hydrocarbon feed mixture. As such, one skilled in the art were conventionally advised to prevent accidental $O_2$ ingress into an alkyne converter, and never encouraged to intentionally introduce molecular $O_2$ into any alkyne converter, during operation where large quantity of hydrocarbons and molecular hydrogen are supplied into the converter.

Thus, it was totally surprising that by intentionally introducing molecular $O_2$, via a stream of compressed air in this Example 1, into the first FEAC along with the hydrocarbon mixture feed, at a very small quantity, e.g., at an $O_2$ concentration ≤70 ppm by mole, based on the total moles of the molecular-oxygen-containing feed mixture at the inlet to the FEAC, even for a short duration of only several minutes, the converting catalyst was actually significantly enhanced in its activity afterwards. In effect, by doing so, we achieved online, in-situ regeneration of a contaminated converting catalyst, resulting in very substantial activity restoration, which was preserved for a long period of time. This indicates that the molecular oxygen did not result in a net effect of oxidizing the active Pd sites on the converting catalyst, which would have resulted in reduction of catalyst activity, contrary to previous concern of oxygen in the feed as a catalyst poison. Moreover, we found that by controlling the amount of molecular oxygen into the converter, e.g., by controlling the flow rate of the molecular-oxygen-containing gas stream, and/or concentration of molecular oxygen in the molecular-oxygen-containing gas stream, such regeneration effect can be achieved without producing a high quantity of $CO_2$ in the converted effluent that would result in $CO_2$ concentration in downstream products, such as the ethylene product, exceeding required specification. From this Example 1, we conclude that with respect to a feed mixture to an alkyne converter comprising high level of a poison (e.g., $AsH_3$ at ≥1 ppb, ≥2 ppb, ≥3 ppb, ≥4 ppb, ≥5 ppb, ≥6 ppb, ≥7 ppb, ≥8 ppb, ≥9 ppb, and ≥10 ppb), implementing one of more of the following can be beneficial to preserve or regain a high performance of the converting catalyst, or achieve a long service life of the converting catalyst: (i) a prolonged oxidation interval with or without a previous or subsequent hydrogenation interval; and (ii) multiple oxidation intervals with various durations between hydrogenation intervals with various durations.

In addition, we have surprisingly found that introducing molecular oxygen into the first FEAC along with the hydrocarbon feed mixture, even at the low levels of concentrations as described above, at the beginning phase of the operation cycle of a converting catalyst, i.e., immediately or shortly after the startup of a newly installed fixed bed of the converting catalyst, fresh and/or regenerated, is particularly beneficial in protecting the converting catalyst from poison contamination, maintaining an extended period of high catalyst activity, and prolonging its service life. If the beginning phase is a hydrogenation interval with no intentional introduction of molecular oxygen into the FEAC as is typically implemented in the prior art, the converting catalyst can experience a fast deactivation, particularly (but not necessarily) if the feed mixture comprises poison(s) at appreciable levels (e.g., $AsH_3$ at ≥1 ppb, ≥2 ppb, ≥3 ppb, ≥4 ppb, ≥5 ppb, ≥6 ppb, ≥7 ppb, ≥8 ppb, ≥9 ppb, and ≥10 ppb). Without intending to be bound by a particular theory, it is believed that during the beginning phase, the converting catalyst has many active sites available and hence a high activity, and therefore tends to adsorb and react with the poison(s) in the feed mixture more readily than later in life, resulting in a high rate of deactivation in a hydrogenation interval. With continuous or intermittent introduction of molecular oxygen into the converter during the beginning phase, as indicated above, the poison can be preferentially oxidized by the molecular oxygen (e.g., on contacting the active site), preventing at least a portion of it from binding with and inactivating active catalyst sites. As such, the high initial activity of the fresh/regenerated converting catalyst can be preserved for a prolonged period of time, the deactivation rate of the converting catalyst is reduced, and the overall service life of the converting catalyst bed can be significantly extended. The beginning phase, calculated from the startup of the reactor with a fresh and/or regenerated converting catalyst load, during which the inventive introduction of molecular oxygen into the converter can range from, e.g., 1, 2, 3, 4, 5, 6, or 7 days to 2, 3, or 4 weeks, to 2, 3, 4, 5, or 6 months.

Example 2

A second FEAC comprising a fixed bed of Pd-containing converting catalyst was monitored, studied, and tested. In an initial hydrogenation interval, a hydrocarbon feed mixture stream comprising methane, ethane, ethylene, propane, propylene, molecular hydrogen, from 100 to 250 ppm by mole of CO, <4000 ppm by mole of acetylene, ≤7.5 ppm of molecular oxygen, and negligible amount, if any, of $AsH_3$ was fed through the inlet into the second FEAC. A converted effluent exiting the converter comprised acetylene at a lower concentration than the feed mixture. The inlet temperature was adjusted to maintain a substantially stable, desired acetylene concentration in the converted effluent in this Example 2. Given the low $AsH_3$ concentration in the feed mixture to the tested FEAC, it is believed that arsenic poisoning of the converting catalyst in the second FEAC reactor was negligible. Before the tests in this Example 2, no molecular-oxygen-containing gas stream was intentionally fed into the second FEAC, i.e., the second FEAC had been operated under hydrogenation interval conditions. As was normal, before the test, the converting catalyst in the second FEAC underwent gradual deactivation, which was compensated by a gradually increased inlet temperature through the production campaign. Without intending to be bound by a particularly theory, it was believed that the catalyst deactivation was due to accumulation of contaminants such as heavy hydrocarbons, N-containing species, P-containing species, and S-containing species. An end of life for the converting catalyst was projected to be Day X in the foreseeable future when the test of this Example 2 started.

Test 2A (First Oxidation Interval)

At the end of a first hydrogenation interval when the inlet temperature of the second FEAC was T1, an air stream was introduced into the hydrocarbon feed mixture, resulting in molecular oxygen concentration in the total feed stream entering the second FEAC of about 10-20 ppm by mole, initiating a first oxidation interval, which continued for about 6 hours. Afterwards the air stream was shut off, while the hydrocarbon feed mixture feed stream continued, ending the first oxidation interval and beginning a second hydrogenation interval. It was observed that at the beginning of the second hydrogenation interval, the inlet temperature was about 7° F. (4° C.) lower than T1, a significant decrease compared to the end of the first hydrogenation interval. The reduced inlet temperature during the second hydrogenation interval was maintained for a prolonged period without abrupt increase, indicating that the converting catalyst was regenerated to some extent during the first oxidation interval, and the regeneration effect maintained for a significant period of time. It was also observed that at the beginning of the second hydrogenation interval, the selectivity of the converting catalyst for hydrogenating acetylene to ethylene increased compared to the end of the first hydrogenation interval. This indicated that the molecular oxygen fed into the second FEAC did not result in net oxidation of the active Pd sites of the converting catalyst, which would otherwise have reduced the activity of the converting catalyst after the first oxidation interval.

Test 2B (Second Oxidation Interval)

At the end of the second hydrogenation interval when the inlet temperature of the second FEAC was T2, an $O_2/N_2$ mixture stream comprising 8 mol % $O_2$ and balance $N_2$ was introduced into the hydrocarbon feed mixture at a flow rate to result in molecular oxygen concentration in the total feed stream entering the second FEAC of about 0.6 ppm by weight (assuming no consumption of molecular oxygen before entering the second FEAC, as in the subsequent tests), initiating a second oxidation interval, which continued for 30 minutes. Afterwards the $O_2/N_2$ mixture stream was shut off, while the hydrocarbon feed mixture feed stream continued, ending the second oxidation interval and beginning a third hydrogenation interval. It was observed that at the beginning of the third hydrogenation interval, the inlet temperature was about 1-2° F. (0.6-1° C.) lower than T2, indicating that the converting catalyst was further regenerated to a certain extent from the second oxidation interval. No $CO_2$ concentration increase was observed in the downstream ethylene product stream produced from the converted effluent exiting the second FEAC. Without intending to be bound by a particular theory, it is believed that the small amount of $CO_2$ produced in the second oxidation interval may have been adsorbed by the converting catalyst.

Test 2C (Third Oxidation Interval)

At the end of the third hydrogenation interval when the inlet temperature of the second FEAC was T3, the $O_2/N_2$ mixture stream used in Test 2B above was introduced into the hydrocarbon feed mixture at a flow rate to result in a molecular oxygen concentration in the total feed stream entering the second FEAC of about 1.2 ppm by weight, initiating a third oxidation interval, which continued for 60 minutes. Afterwards the $O_2/N_2$ mixture stream was shut off, while the hydrocarbon feed mixture feed stream continued, ending the third oxidation interval and beginning a fourth hydrogenation interval. It was observed that at the beginning of the fourth hydrogenation interval, the inlet temperature was about 1-2° F. (0.6-1° C.) lower than T3, indicating that the converting catalyst was further regenerated to a certain extent from the third oxidation interval. A peak $CO_2$ concentration increase of about 0.5 ppm by weight, based on the total weight of the stream at issue, was observed in the downstream ethylene product stream produced from the converted effluent exiting the second FEAC, which was well within the required specification of the ethylene product stream.

Test 2D (Fourth Oxidation Interval)

At the end of the fourth hydrogenation interval when the inlet temperature of the second FEAC was T4, the $O_2/N_2$ mixture stream used in Test 2B above was introduced into the hydrocarbon feed mixture at the same flow rate in Test 2B, resulting in molecular oxygen concentration in the total feed stream entering the second FEAC of about 0.6 ppm by weight, initiating a fourth oxidation interval, which continued for 30 minutes. Afterwards the $O_2/N_2$ mixture stream was shut off, while the hydrocarbon feed mixture feed stream continued, ending the fourth oxidation interval and beginning a fifth hydrogenation interval. Test 2D was essentially a repetition of Test 2B. Again, no $CO_2$ concentration increase was observed in the downstream ethylene product stream produced from the converted effluent exiting the second FEAC.

Test 2E (Fifth Oxidation Interval)

At the end of the fifth hydrogenation interval when the inlet temperature of the second FEAC was T5, the $O_2/N_2$ mixture stream used in Test 2B above was introduced into the hydrocarbon feed mixture the same flow rate in Test 2B, resulting in molecular oxygen concentration in the total feed stream entering the second FEAC of about 0.6 ppm by weight, initiating a fifth oxidation interval, which continued for 8 hours. Afterwards the $O_2/N_2$ mixture stream was shut off, while the hydrocarbon feed mixture feed stream continued, ending the fifth oxidation interval and beginning a sixth hydrogenation interval. It was observed that at the beginning of the sixth hydrogenation interval, the inlet temperature was about 1° F. (0.6° C.) lower than T5, indicating that the converting catalyst was further regenerated to a certain extent from the fifth oxidation interval. A peak $CO_2$ concentration increase of about 200 ppb by weight, based on the total weight of the stream at issue, was observed in the downstream ethylene product stream produced from the converted effluent exiting the second FEAC, which was well within the required specification of the ethylene product stream.

Test 2F (Sixth Oxidation Interval)

At the end of the sixth hydrogenation interval when the inlet temperature of the second FEAC was T6, the $O_2/N_2$ mixture stream used in Test 2B above was introduced into the hydrocarbon feed mixture at the same flow rate in Test 2B, resulting in molecular oxygen concentration in the total feed stream entering the second FEAC of about 0.6 ppm by weight, initiating a sixth oxidation interval, which continued for 8 hours. Afterwards the $O_2/N_2$ mixture stream was shut off, while the hydrocarbon feed mixture feed stream continued, ending the sixth oxidation interval and beginning a seventh hydrogenation interval. Test 2F was essentially a repetition of Test 2E. It was observed that at the beginning of the seventh hydrogenation interval, the inlet temperature was about 1-2° F. (0.6-1° C.) lower than T6, indicating that the converting catalyst was further regenerated to a certain extent from the sixth oxidation interval. A peak $CO_2$ concentration increase which plateaued at 200 to 250 ppb by weight, based on the total weight of the stream at issue, was observed in the downstream ethylene product stream produced from the converted effluent exiting the second FEAC, which was well within the required specification of the ethylene product stream.

Test 2G (Seventh Oxidation Interval)

At the end of the seventh hydrogenation interval when the inlet temperature of the second FEAC was T7, the $O_2/N_2$ mixture stream used in Test 2B above was introduced into the hydrocarbon feed mixture at a flow rate to result in molecular oxygen concentration in the total feed stream entering the second FEAC of about 1.2 ppm by weight, initiating a seventh oxidation interval, which continued for 4 hours. Afterwards the $O_2/N_2$ mixture stream was shut off, while the hydrocarbon feed mixture feed stream continued, ending the seventh oxidation interval and beginning an eighth hydrogenation interval. It was observed that at the beginning of the eighth hydrogenation interval, the inlet temperature was about 6° F. (3° C.) lower than T7, a substantial decrease compared to the end of the seventh hydrogenation interval, indicating that the converting catalyst was further regenerated to a certain extent from the seventh oxidation interval. A peak $CO_2$ concentration increase which plateaued at about 2400 ppb by weight, based on the total weight of the stream at issue, was observed in the downstream ethylene product stream produced from the converted effluent exiting the second FEAC, which was well within the required specification of the ethylene product stream.

Test 2H (Eighth Oxidation Interval)

At the end of the eighth hydrogenation interval when the inlet temperature of the second FEAC was T8, the $O_2/N_2$ mixture stream used in Test 2B above was introduced into the hydrocarbon feed mixture at a flow rate to result in molecular oxygen concentration in the total feed stream entering the second FEAC of about 1.4 ppm by weight, initiating an eighth oxidation interval, which continued for 11 hours. Afterwards the $O_2/N_2$ mixture stream was shut off, while the hydrocarbon feed mixture feed stream continued, ending the eighth oxidation interval and beginning a ninth hydrogenation interval. It was observed that at the beginning of the ninth hydrogenation interval, the inlet temperature was about 14° F. (8° C.) lower than T8, a very significant decrease compared to the end of the eighth hydrogenation interval, indicating that the converting catalyst was further regenerated to a certain extent from the eighth oxidation interval. A peak $CO_2$ concentration increase which plateaued at about 2900 ppb by weight, based on the total weight of the stream at issue, was observed in the downstream ethylene product stream produced from the converted effluent exiting the second FEAC, which was well within the required specification of the ethylene product stream. Subsequently, the production rate during the ninth hydrogenation interval, which lasted about 15.5 hours, increased slightly, resulting an inlet temperature increase of about 6° F. (3° C.).

Test 2I (Ninth Oxidation Interval)

At the end of the ninth hydrogenation interval when the inlet temperature of the second FEAC was T9, the $O_2/N_2$ mixture stream used in Test 2B above was introduced into the hydrocarbon feed mixture at a flow rate to result in molecular oxygen concentration in the total feed stream entering the second FEAC of about 1.4 ppm by weight, initiating a ninth oxidation interval, which continued for 11 hours. Afterwards the $O_2/N_2$ mixture stream was shut off, while the hydrocarbon feed mixture feed stream continued, ending the ninth oxidation interval and beginning a tenth hydrogenation interval. It was observed that at the beginning of the tenth hydrogenation interval, the inlet temperature was about 8° F. (4° C.) lower than T9, a very significant decrease compared to the end of the ninth hydrogenation interval, indicating that the converting catalyst was further regenerated to a certain extent from the ninth oxidation interval. A peak $CO_2$ concentration increase which plateaued at about 3000 ppb by weight, based on the total weight of the stream at issue, was observed in the downstream ethylene product stream produced from the converted effluent exiting the second FEAC, which was well within the required specification of the ethylene product stream.

These tests in this Example 2 clearly showed that supplying a molecular oxygen-containing gas stream to the second FEAC at a low molecular oxygen concentration in the total feed into the second FEAC at, e.g., about 0.5 to 1.5 ppm by weight, based on the total weight of the total feeds fed into the second FEAC, was effective to cause desirable reaction(s) on the converting catalyst resulting in substantial regeneration. Multiple short-duration oxidation intervals implemented between hydrogenation intervals produced a cumulated inlet temperature decrease, which was very significant and maintained for a long period of time after the completion of the tests. Surprisingly, the regeneration effect resulting from the multiple oxidation intervals, manifested by increased catalyst activity and improved selectivity for desired reactions, was projected to extend the run-length of the converting catalyst in the second FEAC by multiple months beyond the end of life (Day X as discussed earlier) originally projected before the tests started, which translates to very substantial value of additional amounts of valuable products such as ethylene and propylene to be produced from the converting catalyst. Additional implementation of additional oxidation intervals in the future may further extend the service life of the converting catalyst in the second FEAC beyond the previously projected Day X.

These tests indicated that only a portion (about 15-55%) of the molecular oxygen introduced into the second FEAC was converted into $CO_2$. The $CO_2$ may be produced by the oxidation of CO present in the hydrocarbon feed mixture, coke and heavy hydrocarbons present on the converting catalyst, and other hydrocarbons present in the hydrocarbon feed. A portion of the molecular oxygen fed into the FEAC is believed to have been consumed by the oxidation of the molecular hydrogen present in the hydrocarbon feed mixture. As such, molecular oxygen can be continuously fed into the FEAC at concentrations highly effective in regenerating the converting catalyst for an extended oxidation interval without resulting in substantial increase of $CO_2$ concentration in the downstream ethylene product stream to a level beyond the product specification. Since the overall amount of molecular oxygen fed into the FEAC was small, the amount of water produced was small, which can be conveniently abated in a downstream drier using, e.g., a desiccant.

The tests also showed that by feeding the molecular oxygen into the FEAC at the indicated concentrations for extended oxidation intervals, no significant or abrupt exotherm was observed from the second FEAC. Thus, the processes of this disclosure can be conducted safely, contrary to previous concerns in the industry.

While the Examples of this disclosure were processes conducted in a FEAC, it is believed that the same or similar processes can be implemented in a back-end acetylene converter, a MAPD converter, or any other reactor in which an alkyne is converted into an olefin in the presence of a converting catalyst prone to gradual loss of activity through prolonged hydrogenation operations, with the same or similar benefits. The converting catalysts in such other reactors can be regenerated in-situ and online, without interrupting the production of valuable products, and in certain embodiments, without sacrificing the product quality.

Traditional regeneration of the converting catalyst used in an alkyne converter requires the shutdown of the alkyne converter. In case of ex-situ regeneration, taking the used catalyst out of the converter, loading the used catalyst in a regenerator vessel, and then exposing the used catalyst to high-concentration of molecular oxygen at an elevated temperature to remove coke and heavy hydrocarbons on the used catalyst. Upon such high-severity treatment and cooling, the regenerated converting catalyst can be taken out of the regenerator, and then reloaded into an alkyne converter. In case of in-situ regeneration, the converter is then connected to the regeneration equipment, a molecular oxygen-containing gas such as air is fed into the converter to contact the used converting catalyst at an elevated temperature to remove coke and heavy hydrocarbons on the used catalyst. Such regeneration activities are very time consuming, difficulty to manage, and costly compared to the online regeneration processes of this disclosure. Indeed, it is very surprising that by exposing the converting catalyst to a low concentration of molecular oxygen in the feed mixture, traditionally considered as a catalyst poison, one can achieve such substantial enhancement of the activity of the converting catalyst. The fact that such enhancement can be achieved without interrupting production of quality products can translates to very substantial cost savings to the olefins recovery process in an olefins production plant.

All patents, test procedures, and other documents cited herein, including priority documents, are fully incorporated by reference to the extent such disclosure is not inconsistent. It is not intended that the scope of the claims appended hereto be limited to the descriptions set forth herein but rather that the claims be construed as encompassing all patentable features which reside herein, including all features which would be treated as equivalents thereof by those skilled in the relevant art. When lower and upper limits are specified, ranges from any lower limit to any upper limit are expressly within the scope of the invention. The term "comprising" is synonymous with the term "including." When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa. Pressure values are absolute (bar, kPa, psi, or psia) unless expressly indicated as gauge (barg, kPag, psig).

This disclosure can include one or more of the following aspects/embodiments.

A1. A process for converting an alkyne to an olefin, the process comprising:
 (I) during a first hydrogenation interval, supplying a feed mixture into a converting zone through a feed inlet, where the feed mixture comprises the alkyne, the olefin, and molecular hydrogen, and the feed mixture is essentially free of molecular oxygen;
 (II) during the first hydrogenation interval, contacting the feed mixture with a converting catalyst comprising a hydrogenation metal (preferably Pd) under converting conditions in the converting zone to convert at least a portion of the alkyne to the olefin to produce a first converted effluent exiting the converting zone;
 (III) during an oxidation interval after the first hydrogenation interval, supplying a molecular-oxygen-containing gas stream and the feed mixture into the converting zone; and
 (IV) during the oxidation interval, contacting the feed mixture and the molecular oxygen with the converting catalyst in the converting zone to enhance the converting catalyst and to produce a second converted effluent exiting the converting zone.

A2. The process of A1, wherein the molecular-oxygen-containing gas stream is selected from (a) pure $O_2$; (b) pure $O_3$; (c) air; (d) a mixture of $O_2$ and/or $O_3$ with one or more inert gas; and (e) a mixture of two or more of (a), (b), (c), and (d).

A3. The process of A1 or A2, wherein the molecular-oxygen-containing gas stream comprises $O_2$ at a concentration in a range from 5 to 25 mol %, based on the total moles of gases in the molecular-oxygen-containing gas stream.

A4. The process of any of A1 to A3, wherein the oxidation interval ranges from 1 minute to 48 hours, preferably from 5 minutes to 24 hours, preferably from 1 hour to 12 hours.

A5. The process of any of A1 to A4, wherein in step (III), the molecular-oxygen-containing gas stream is mixed with the feed mixture to form an oxygen-containing feed mixture, and the oxygen-containing feed mixture is then supplied into the converting zone through the feed inlet.

A6. The process of any of A1 to A6, wherein a quantity of the molecular-oxygen-containing gas stream corresponding to a molecular oxygen concentration in a range from 0.25 to 30 ppm (preferably from 1 to 20 ppm, preferably from 1 to 10 ppm) by mole, on the basis of the total moles of molecules in the feed mixture, is supplied into the converting zone.

A7. The process of any of A1 to A6, further comprising:
(V) during the first hydrogenation interval, monitoring the performance of the converting catalyst; and
(VI) stopping the first hydrogenation interval when an unexpected decrease of performance of the converting catalyst is observed in step (V).

A8. The process of A7, wherein the unexpected decrease of performance of the converting catalyst comprises one or more of:
(a) an increase of inlet temperature of ≥5° C. within a period of ≤24 hours while maintaining substantially constant alkyne concentration in the first converted effluent; and
(b) a temperature excursion resulting in reactor trip.

A9. The process of A7 or A8, wherein immediately after step (VI), the oxidation interval and steps (III) and (IV) are started.

A10. The process of A7 or A8, wherein after step (VI), and before the oxidation interval and steps (III) and (IV) are started, during an interruption interval, steps (I) and (III) are not carried out.

A11. The process of any of A1 to A10, wherein steps (III) and (IV) are carried out after the converting catalyst has passed 50% of a normal run of the converting catalyst.

A12. The process of any of A1 to A11, wherein the feed mixture in step (I) comprises arsenic at a concentration of at least 2 ppb by mole, expressed as the mole concentration of $AsH_3$ on the basis of the total moles in the feed mixture.

A13. The process of any of A1 to A12, further comprising:
producing an olefin product consisting essentially of the olefin and optionally $CO_2$ at a $CO_2$ concentration no greater than a specification level from the first converted effluent or the second converted effluent;
wherein both the first converted effluent and the second converted effluent comprise $CO_2$ at concentrations no higher than a threshold level that would result in the olefin product comprising $CO_2$ above the specification level.

A14. The process of any of A1 to A13, wherein step (I) is carried out at a first inlet temperature of $T(1)°$ C., and step (III) is carried out at a second inlet temperature of $T(2)°$ C., and $0 \leq T(1)-T(2) \leq 12$, preferably $1 \leq T(1)-T(2) \leq 10$, preferably $1 \leq T(1)-T(2) \leq 8$, preferably $1 \leq T(1)-T(2) \leq 6$, preferably $1 \leq T(1)-T(2) \leq 5$, preferably $1 \leq T(1)-T(2) \leq 4$, preferably $1 \leq T(1)-T(2) \leq 3$.

A15. The process of any of A1 to A14, further comprising:
(VII) after the oxidation interval, starting a second hydrogenation interval and supplying the feed mixture into the converting zone through the feed inlet and contacting the feed mixture with the converting catalyst under converting conditions in the converting zone to produce a third converted effluent exiting the converting zone.

A16. The process of A15, wherein at the beginning of the second hydrogenation interval, the converting catalyst exhibits a higher activity than at the end of the first hydrogenation interval.

A17. The process of A16, wherein:
at the end of the first hydrogenation interval, the feed mixture at the feed inlet has a temperature of Ta ° C. to maintain a threshold concentration of the alkyne in the first converted effluent;
at the beginning of the second hydrogenation interval, the feed mixture at the feed inlet has a temperature of Tb ° C. to maintain the threshold concentration of the alkyne in the third converted effluent; and
Ta−Tb≥1; preferably Ta−Tb≥2; preferably Ta−Tb≥3; preferably Ta−Tb≥4; preferably Ta−Tb≥5; preferably Ta−Tb≥6; preferably Ta−Tb≥7; preferably Ta−Tb≥8; preferably Ta−Tb≥9; preferably Ta−Tb≥10.

A18. The process of any of A15 to A17, wherein at the beginning of the second hydrogenation interval, the converting catalyst exhibits a higher selectivity for converting the alkyne to the olefin than at the end of the first hydrogenation interval.

A19. The process of any of A1 to A18, wherein the feed mixture consists essentially of C1-C3 hydrocarbons and molecular hydrogen.

A20. The process of any of A1 to A19, wherein the alkyne is acetylene, the olefin is ethylene, and the converting zone is located in a front-end acetylene converter.

A21. The process of A19 or A20, wherein the feed mixture comprises propane, propylene, and propadiene.

A22. The process of A198 or A20, wherein the feed mixture is substantially free of C3+ hydrocarbons.

A23. The process of any of A1 to A19, wherein the alkyne is acetylene, the olefin is ethylene, and the converting zone is located in a back-end acetylene converter, and step (I) comprises:
(Ia) providing a C2 hydrocarbon stream; and
(Ib) supplying molecular hydrogen into the C2 hydrocarbon stream to form the feed mixture.

A24. The process of A23, wherein in step (Ib) the molecular hydrogen is supplied at a molar quantity substantially equal to the molar quantity of acetylene in the C2 hydrocarbon stream.

A25. The process of any of A1 to A19, wherein the alkyne is methylacetylene, the olefin is propylene, and the converting zone is located in a methylacetylene-propadiene converter, and step (I) comprises:
(Ic) providing a C3 hydrocarbon stream comprising propane, propylene, and propadiene; and
(Id) supplying molecular hydrogen into the C3 hydrocarbon stream to form the feed mixture.

A26. The process of A25, wherein in step (Id) the molecular hydrogen is supplied at a molar quantity substantially equal to the total molar quantity of methylacetylene and propadiene combined in the C3 hydrocarbon stream.

A27. The process of any of A1 to A26, wherein before starting step (III), the converting catalyst is contaminated by one or more of coke, a heavy hydrocarbon, a poison comprising one or more of: arsenic and/or a compound thereof (e.g., $AsH_3$), mercury and/or a compound thereof, a nitrogen-containing compound (e.g., amines), a phosphorous-containing compound (e.g., a phosphine), a sulfur-containing compound (e.g., COS, $H_2S$, and $CH_3SH$), a halogen-containing compound (e.g., a chlorine-containing compound), a transition metal (e.g., Fe, Mn, Pb, Ti) and/or a compound thereof, an alkali metal (e.g., Li, Na, K) and/or a compound thereof, and an alkaline earth metal (e.g., Mg, Ca) and/or a compounds thereof.

A28. The process of any of A1 to A24, wherein the converting catalyst further comprises a support material selected from alumina, silica, zirconia, titania, thoria, alkaline earth oxides, rare earth oxides, and mixtures, composites, and compounds of at least two thereof.

A29. The process of any of A1 to A28, wherein steps (III) and (IV) are carried out in a beginning phase of an operation cycle.

B1. A process for converting an alkyne to an olefin, the process comprising:
(i) supplying a feed mixture comprising the alkyne, the olefin, an optional catalyst poison, and molecular hydrogen into a converting zone;
(ii) supplying a molecular-oxygen-containing gas stream into the converting zone;
(iii) contacting the feed mixture and the molecular oxygen with the converting catalyst in the converting zone under converting conditions to produce a converted effluent exiting the converting zone and to prevent, reduce, or delay the contamination of the converting catalyst by one or more of coke, a heavy hydrocarbon, and the optional catalyst poison.

B2. The process of B1, wherein the catalyst poison is present in the feed mixture, and is selected from arsenic and/or a compound thereof (e.g., $AsH_3$); mercury and/or a compound thereof; a nitrogen-containing compound (e.g., amines); a phosphorous-containing compound (e.g., a phosphine); a sulfur-containing compound (e.g., COS, $H_2S$, and $CH_3SH$); a halogen-containing compound (e.g., a chlorine-containing compound); a transition metal (e.g., Fe, Mn, Pb, Ti) and/or a compound thereof; an alkali metal (e.g., Li, Na, K) and/or a compound thereof; and an alkaline earth metal (e.g., Mg, Ca) and/or a compounds thereof; and mixtures and combinations thereof.

B3. The process of B2, wherein the catalyst poison comprises an arsenic-containing compound.

B4. The process of B3, wherein the catalyst poison comprises the arsenic-containing compound at a concentration of at least 2 ppb by mole, expressed as the mole concentration of $AsH_3$ on the basis of the total moles in the feed mixture.

B5. The process of any of B1 to B4, wherein the converting catalyst comprises a hydrogenation metal, preferably Pd.

B6. The process of any of B1 to B5, wherein the molecular-oxygen-containing gas stream is selected from (a) pure $O_2$; (b) pure $O_3$; (c) air; (d) a mixture of $O_2$ with one or more inert gas; and (e) a mixture of two or more of (a), (b), (c), and (d).

B7. The process of any of B1 to B6, wherein the molecular-oxygen-containing gas stream comprises $O_2$ at a concentration in a range from 5 to 25 mol %, based on the total moles of gases in the molecular-oxygen-containing gas stream.

B8. The process of any of B1 to B7, wherein the molecular-oxygen-containing gas stream is mixed with the feed mixture to form an oxygen-containing feed mixture, and the oxygen-containing feed mixture is then supplied into the converting zone.

B9. The process of any of B1 to B8, wherein a quantity of the molecular-oxygen-containing gas stream corresponding to a molecular oxygen concentration in a range from 0.25 to 30 ppm (preferably from 1 to 20 ppm, preferably from 1 to 10 ppm) by mole, on the basis of the total moles of molecules in the feed mixture, is supplied into the converting zone.

B10. The process of any of B1 to B9, wherein in steps (ii) and (iii) are carried out after the converting catalyst has passed 50% of a normal run of the process.

B11. The process of any of B1 to B10, further comprising:
producing an olefin product consisting essentially of the olefin and optionally $CO_2$ at a $CO_2$ concentration no greater than a specification level from the converted effluent;
wherein the second converted effluent comprise $CO_2$ at concentrations no higher than a threshold level that would result in the olefin product comprising $CO_2$ above the specification level.

B12. The process of any of B1 to B11, wherein the feed mixture consists essentially of C1-C3 hydrocarbons and molecular hydrogen.

B13. The process of any of B1 to B12, wherein the alkyne is acetylene, the olefin is ethylene, and the converting zone is located in a front-end acetylene converter.

B14. The process of B12 or B13, wherein the feed mixture comprises propane, propylene, and propadiene.

B15. The process of B12 or B13, wherein the feed mixture is substantially free of C3+ hydrocarbons.

B16. The process of any of B1 to B15, wherein the alkyne is acetylene, the olefin is ethylene, and the converting zone is located in a back-end acetylene converter, and step (i) comprises:
(ia) providing a C2 hydrocarbon stream; and
(ib) supplying molecular hydrogen into the C2 hydrocarbon stream to form the feed mixture.

B17. The process of B16, wherein in step (ib) the molecular hydrogen is supplied at a molar quantity substantially equal to the molar quantity of acetylene in the C2 hydrocarbon stream.

B18. The process of any of B1 to B17, wherein the alkyne is methylacetylene, the olefin is propylene, and the converting zone is located in a methylacetylene-propadiene converter, and step (i) comprises:
(ic) providing a C3 hydrocarbon stream comprising propane, propylene, and propadiene; and
(id) supplying molecular hydrogen into the C3 hydrocarbon stream to form the feed mixture.

B19. The process of B18, wherein in step (id) the molecular hydrogen is supplied at a molar quantity substantially equal to the total molar quantity of methylacetylene and propadiene combined in the C3 hydrocarbon stream.

B20. The process of any of B1 to B19, further comprising:
(iv) stopping steps (ii) and (iii) at the end of an oxidation interval; and
(v) after the oxidation interval and step (iv), starting a hydrogenation interval, and contacting the feed mixture with the converting catalyst in the converting zone to produce another converted effluent.

B21. The process of any of B1 to B20, wherein steps (i), (ii), and (iii) are carried out during a beginning phase of an operation cycle.

B22. The process of B21, wherein steps (ii) and (iii) are carried out intermittently or continuously during the beginning phase of the operation cycle.

C1. A process for converting an alkyne to an olefin, the process comprising:
(1) supplying a feed mixture comprising the alkyne, the olefin, and molecular hydrogen into a converting zone;
(2) during an oxidation interval, supplying a molecular-oxygen-containing gas stream into the converting zone; and
(3) during the oxidation interval, contacting the feed mixture and the molecular oxygen with a converting catalyst in the converting zone, wherein the converting catalyst is contaminated by one or more of coke, a heavy hydrocarbon, a poison comprising one or more of: arsenic and/or a compound thereof (e.g., $AsH_3$), mercury and/or a compound thereof, a nitrogen-containing compound (e.g., amines), a phosphorous-containing compound (e.g., a phosphine), a sulfur-containing compound (e.g., COS, $H_2S$, and $CH_3SH$), a halogen-containing compound (e.g., a chlorine-containing compound), a transition metal (e.g., Fe, Mn, Pb, Ti) and/or a compound thereof, an alkali metal (e.g., Li, Na, K) and/or a compound thereof, and an alkaline earth metal (e.g., Mg, Ca) and/or a compounds thereof, to convert at least a portion of the alkyne to the olefin, and to enhance the converting catalyst.

C2. The process of C1, wherein the converting catalyst comprises a hydrogenation metal, preferably Pd.

C3. The process of C1 or C2, wherein the molecular-oxygen-containing gas stream is selected from (a) pure $O_2$; (b) pure $O_3$; (c) air; (d) a mixture of $O_2$ with one or more inert gas; and (e) a mixture of two or more of (a), (b), (c), and (d).

C4. The process of any of C1 to C6, wherein the molecular-oxygen-containing gas stream comprises $O_2$ at a concentration in a range from 5 to 25 mol %, based on the total moles of gases in the molecular-oxygen-containing gas stream.

C5. The process of any of C1 to C4, wherein the molecular-oxygen-containing gas stream is mixed with the feed mixture to form an oxygen-containing feed mixture, and the oxygen-containing feed mixture is then supplied into the converting zone.

C6. The process of any of C1 to C5, wherein a quantity of the molecular-oxygen-containing gas stream corresponding to a molecular oxygen concentration in a range from 0.25 to 30 ppm (preferably from 1 to 20 ppm, preferably from 1 to 10 ppm) by mole, on the basis of the total moles of molecules in the feed mixture, is supplied into the converting zone.

C7. The process of any of C1 to C6, wherein in steps (ii) and (iii) are carried out after the converting catalyst has passed 50% of a normal run of the process.

C8. The process of any of C1 to C7, further comprising:
producing an olefin product consisting essentially of the olefin and optionally $CO_2$ at a $CO_2$ concentration no greater than a specification level from the converted effluent;
wherein the second converted effluent comprise $CO_2$ at concentrations no higher than a threshold level that would result in the olefin product comprising $CO_2$ above the specification level.

C9. The process of any of C1 to C8, wherein the feed mixture consists essentially of C1-C3 hydrocarbons and molecular hydrogen.

C10. The process of any of C1 to C9, wherein the alkyne is acetylene, the olefin is ethylene, and the converting zone is located in a front-end acetylene converter.

C11. The process of C1 to C10, wherein the feed mixture comprises propane, propylene, and propadiene.

C12. The process of C1 to C11, wherein the feed mixture is substantially free of C3+ hydrocarbons.

C13. The process of any of C1 to C12, wherein the alkyne is acetylene, the olefin is ethylene, and the converting zone is located in a back-end acetylene converter, and step (1) comprises:
(1a) providing a C2 hydrocarbon stream; and
(1b) supplying molecular hydrogen into the C2 hydrocarbon stream to form the feed mixture.

C13. The process of C12, wherein in step (1b) the molecular hydrogen is supplied at a molar quantity substantially equal to the molar quantity of acetylene in the C2 hydrocarbon stream.

C14. The process of any of C1 to C13, wherein the alkyne is methylacetylene, the olefin is propylene, and the converting zone is located in a methylacetylene-propadiene converter, and step (1) comprises:
(1c) providing a C3 hydrocarbon stream comprising propane, propylene, and propadiene; and
(1d) supplying molecular hydrogen into the C3 hydrocarbon stream to form the feed mixture.

C15. The process of C14, wherein in step (1d) the molecular hydrogen is supplied at a molar quantity substantially equal to the total molar quantity of methylacetylene and propadiene combined in the C3 hydrocarbon stream.

C16. The process of any of C1 to C15, further comprising:
(4) stopping steps (2) and (3) at the end of an oxidation interval; and
(5) after the oxidation interval and step (4), starting a hydrogenation interval, and contacting the feed mixture with the converting catalyst in the converting zone to produce another converted effluent.

C16. The process of any of C1 to C16, wherein steps (1), (2), and (3) are carried out during a beginning phase of a production cycle.

C17. The process of C16, wherein steps (2) and (3) are carried out during the beginning phase of the production cycle intermittently or continuously.

The invention claimed is:

1. A process for converting an alkyne to an olefin, the process comprising:
   (1) supplying a feed mixture comprising the alkyne, the olefin, and molecular hydrogen into a converting zone;
   (2) supplying a molecular-oxygen-containing gas stream into the converting zone; and
   (3) during an oxidation interval, contacting the feed mixture and the molecular oxygen with a converting catalyst in the converting zone to produce a converted effluent, wherein the converting catalyst is contaminated before the oxidation interval by one or more of coke, a heavy hydrocarbon, a poison comprising one or more of: arsenic and/or a compound thereof, mercury and/or a compound thereof, a nitrogen-containing compound, a phosphorous-containing compound, a sulfur-containing compound, a halogen-containing compound, a transition metal and/or a compound thereof, an alkali metal and/or a a compound thereof, and an alkaline earth metal and/or a compounds thereof, to convert at least a portion of the alkyne to the olefin, and to enhance the activity and/or selectivity of the converting catalyst.

2. The process of claim 1, wherein the converting catalyst comprises a hydrogenation metal.

3. The process of claim 2, wherein the converting catalyst comprises Pd.

4. The process of claim 1, wherein the molecular-oxygen-containing gas stream is selected from (a) pure $O_2$; (b) pure $O_3$; (c) air; (d) a mixture of $O_2$ with one or more inert gas; and (e) a mixture of two or more of (a), (b), (c), and (d).

5. The process of claim 1, wherein the molecular-oxygen-containing gas stream comprises $O_2$ at a concentration in a range from 5 to 25 mol %, based on the total moles of gases in the molecular-oxygen-containing gas stream.

6. The process of claim 1, wherein the molecular-oxygen-containing gas stream is mixed with the feed mixture to form an oxygen-containing feed mixture, and the oxygen-containing feed mixture is then supplied into the converting zone.

7. The process of claim 1, wherein a quantity of the molecular-oxygen-containing gas stream corresponding to a molecular oxygen concentration in a range from 0.25 to 100 ppm by mole, on the basis of the total moles of molecules in the feed mixture, is supplied into the converting zone.

8. The process of claim 1, wherein in steps (ii) and (iii) are carried out in the beginning phase of an operation cycle and/or after the converting catalyst has passed 50% of an operation cycle.

9. The process of claim 1, further comprising:
producing an olefin product consisting essentially of the olefin and optionally $CO_2$ at a $CO_2$ concentration no greater than a specification level from the converted effluent;
wherein the converted effluent comprises $CO_2$ at concentrations no higher than a threshold level that would result in the olefin product comprising $CO_2$ above the specification level.

10. The process of claim 1, wherein the alkyne is acetylene, the olefin is ethylene, and the converting zone is located in a front-end acetylene converter.

11. The process of claim 1, wherein the alkyne is acetylene, the olefin is ethylene, and the converting zone is located in a back-end acetylene converter, and step (1) comprises:
(1a) providing a C2 hydrocarbon stream; and
(1b) supplying molecular hydrogen into the C2 hydrocarbon stream to form the feed mixture, wherein the molecular hydrogen is supplied at a molar quantity substantially equal to the molar quantity of acetylene in the C2 hydrocarbon stream.

12. The process of claim 1, wherein the alkyne is methylacetylene, the olefin is propylene, and the converting zone is located in a methylacetylene-propadiene converter, and step (1) comprises:
(1c) providing a C3 hydrocarbon stream comprising propane, propylene, and propadiene; and
(1d) supplying molecular hydrogen into the C3 hydrocarbon stream to form the feed mixture, wherein the molecular hydrogen is supplied at a molar quantity substantially equal to the total molar quantity of methylacetylene and propadiene combined in the C3 hydrocarbon stream.

13. The process of claim 1, further comprising:
(4) stopping steps (2) and (3) at the end of an oxidation interval; and
(5) after the oxidation interval and step (4), starting a hydrogenation interval, and contacting the feed mixture with the converting catalyst in the converting zone to produce another converted effluent.

14. A process for converting an alkyne to an olefin, the process comprising:
(I) during a first hydrogenation interval, supplying a feed mixture into a converting zone through a feed inlet, where the feed mixture comprises the alkyne, the olefin, and molecular hydrogen, and the feed mixture is essentially free of molecular oxygen;
(II) during the first hydrogenation interval, contacting the feed mixture with a converting catalyst comprising a hydrogenation metal under converting conditions in the converting zone to convert at least a portion of the alkyne to the olefin to produce a first converted effluent exiting the converting zone;
(III) during an oxidation interval after the first hydrogenation interval, supplying a molecular-oxygen-containing gas stream and the feed mixture into the converting zone; and
(IV) during the oxidation interval, contacting the feed mixture and the molecular a oxygen with the converting catalyst in the converting zone to enhance the activity and/or selectivity of the converting catalyst and to produce a second converted effluent exiting the converting zone.

15. The process of claim 14, wherein a quantity of the molecular-oxygen-containing gas stream corresponding to a molecular oxygen concentration in a range from 0.25 to 30 ppm by mole, on the basis of the total moles of molecules in the feed mixture, is supplied into the converting zone.

16. The process of claim 14, further comprising:
(V) during the first hydrogenation interval, monitoring the performance of the converting catalyst; and
(VI) stopping the first hydrogenation interval when an unexpected decrease of performance of the converting catalyst is observed in step (V), wherein the unexpected decrease of performance of the converting catalyst comprises one or more of:
(a) an increase of inlet temperature of $\geq 5°$ C. within a period of $\leq 24$ hours while maintaining substantially constant alkyne concentration in the first converted effluent; and
(b) a temperature excursion resulting in reactor trip.

17. The process of claim 14, further comprising:
producing an olefin product consisting essentially of the olefin and optionally $CO_2$ at a $CO_2$ concentration no greater than a specification level from the first converted effluent or the second converted effluent;
wherein both the first converted effluent and the second converted effluent comprise $CO_2$ at concentrations no higher than a threshold level that would result in the olefin product comprising $CO_2$ above the specification level.

18. The process of claim 14, further comprising:
(VII) after the oxidation interval, starting a second hydrogenation interval and supplying the feed mixture into the converting zone through the feed inlet and contacting the feed mixture with the converting catalyst under converting conditions in the converting zone to produce a third converted effluent exiting the converting zone;
wherein:
at the end of the first hydrogenation interval, the feed mixture at the feed inlet has a temperature of Ta ° C. to maintain a threshold concentration of the alkyne in the first converted effluent;
at the beginning of the second hydrogenation interval, the feed mixture at the feed inlet has a temperature of Tb ° C. to maintain the threshold concentration of the alkyne in the third converted effluent; and
Ta−Tb$\geq$1.

19. The process of claim 14, wherein at the beginning of the second hydrogenation interval, the converting catalyst exhibits a higher selectivity for converting the alkyne to the olefin than at the end of the first hydrogenation interval.

* * * * *